(12) United States Patent
Minami et al.

(10) Patent No.: US 12,115,044 B2
(45) Date of Patent: Oct. 15, 2024

(54) COMPOSITE STRETCHABLE MEMBER MANUFACTURING APPARATUS

(71) Applicant: ZUIKO CORPORATION, Osaka (JP)

(72) Inventors: Asuka Minami, Osaka (JP); Miwa Koshijima, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 402 days.

(21) Appl. No.: 17/610,209

(22) PCT Filed: Apr. 7, 2020

(86) PCT No.: PCT/JP2020/015713
§ 371 (c)(1),
(2) Date: Nov. 10, 2021

(87) PCT Pub. No.: WO2020/230479
PCT Pub. Date: Nov. 19, 2020

(65) Prior Publication Data
US 2022/0218534 A1    Jul. 14, 2022

(30) Foreign Application Priority Data

May 13, 2019    (JP) .................................. 2019-090798

(51) Int. Cl.
*B32B 41/00*    (2006.01)
*A61F 13/15*    (2006.01)
(Continued)

(52) U.S. Cl.
CPC .. *A61F 13/15593* (2013.01); *A61F 13/49011* (2013.01); *A61F 13/15699* (2013.01);
(Continued)

(58) Field of Classification Search
CPC .......... A61F 13/15593; A61F 13/49011; A61F 13/15699; A61F 13/4902; B29C 66/1122; B29L 2031/4878
(Continued)

(56) References Cited

U.S. PATENT DOCUMENTS

2010/0078119 A1    4/2010    Yamamoto
2011/0057012 A1    3/2011    Yamamoto
(Continued)

FOREIGN PATENT DOCUMENTS

| CN | 102209511 | 10/2011 |
|---|---|---|
| CN | 203524862 | 4/2014 |

(Continued)

OTHER PUBLICATIONS

International Search Report issued Jul. 7, 2020 in International (PCT) Application No. PCT/JP2020/015713.
(Continued)

*Primary Examiner* — Michael N Orlando
*Assistant Examiner* — Joshel Rivera
(74) *Attorney, Agent, or Firm* — Wenderoth, Lind & Ponack, L.L.P.

(57) ABSTRACT

Provided is a manufacturing apparatus for manufacturing a composite stretchable member capable of improving a function of preventing cutting by reducing a defect in which an elastic member is detached from a groove of a conveying roller. The manufacturing apparatus includes a guide device that guides the two sheets and the elastic members to a bonding device. The guide device includes a guide member that guides the elastic members to respective multiple grooves on an outer peripheral surface of a conveying roller of the bonding device. The guide member is provided at its leading end with multiple guide grooves for holding the corresponding elastic members. The guide member is dis-
(Continued)

posed to allow the elastic members positioned between the guide grooves and the corresponding grooves of the conveying roller to each have a length of 30 mm or less.

20 Claims, 18 Drawing Sheets

(51) Int. Cl.
    *A61F 13/49*     (2006.01)
    *B29C 65/00*     (2006.01)
    *B29L 31/48*     (2006.01)

(52) U.S. Cl.
    CPC ....... *A61F 13/4902* (2013.01); *B29C 66/1122* (2013.01); *B29L 2031/4878* (2013.01)

(58) Field of Classification Search
    USPC .................... 156/60, 64, 350, 351, 378, 379
    See application file for complete search history.

(56) References Cited

U.S. PATENT DOCUMENTS

| | | |
|---|---|---|
| 2012/0118485 A1 | 5/2012 | Kameda et al. |
| 2016/0242967 A1 | 8/2016 | Wada |
| 2018/0140473 A1 | 5/2018 | Koshijima et al. |
| 2018/0147095 A1 | 5/2018 | Koshijima et al. |
| 2020/0179180 A1 | 6/2020 | Koshijima et al. |

FOREIGN PATENT DOCUMENTS

| | | |
|---|---|---|
| CN | 107848244 | 3/2018 |
| EP | 3 296 100 | 3/2018 |
| JP | 10-179635 | 7/1998 |
| JP | 2006-230834 | 9/2006 |
| JP | 2010-279616 | 12/2010 |
| JP | 2016-78363 | 5/2016 |
| JP | 2019-30441 | 2/2019 |
| WO | 2016/208502 | 12/2016 |
| WO | 2019/003908 | 1/2019 |

OTHER PUBLICATIONS

Extended European Search Report issued Jun. 2, 2022 in European Patent Application No. 20805033.6.
Office Action issued Jun. 21, 2022 in Chinese Patent Application No. 202080035780.7, with English-language translation.
Summary of the Decision of Refusal issued Feb. 20, 2024 in corresponding Japanese Patent Application No. 2021- 519304, with partial English language translation.

FIG. 16
STAGE 1
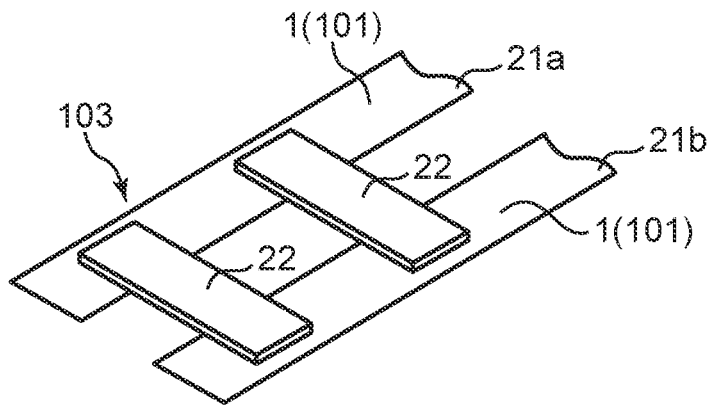
STAGE 2
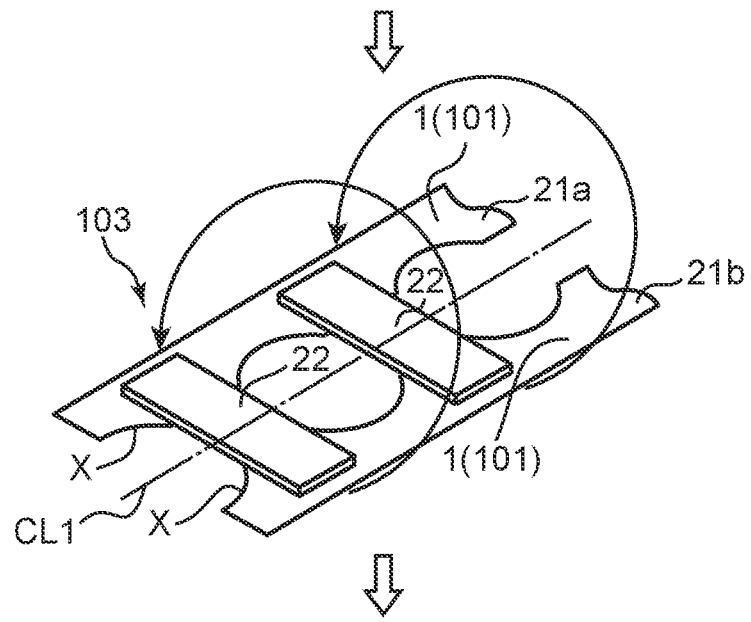
STAGE 3
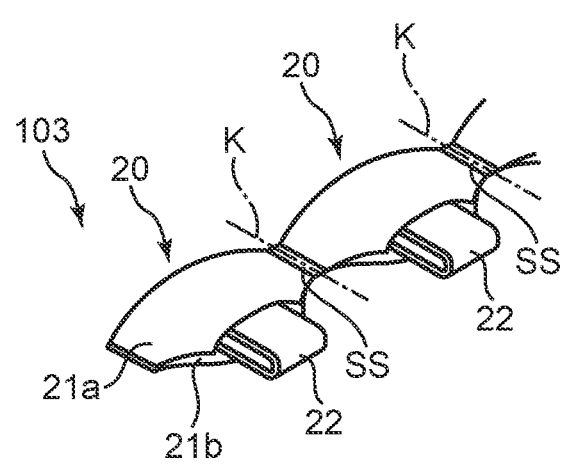

COMPOSITE STRETCHABLE MEMBER MANUFACTURING APPARATUS

TECHNICAL FIELD

The present invention relates to a manufacturing apparatus for manufacturing a composite stretchable member.

BACKGROUND ART

Wearing articles such as a disposable diaper having a waistline portion and a crotch portion have been known. In the wearing article such as the disposable diaper, the waistline portion of the wearing article may be formed of a composite stretchable member, which is stretchable, to improve wearing comfort.

As an apparatus for manufacturing a composite stretchable member, for example, an apparatus described in Patent Literature 1 is known.

The apparatus described in Patent Literature 1 performs welding processing with an elastically stretchable member sandwiched between two sheets made of a nonwoven fabric or the like by feeding these two sheets and the elastically stretchable member to a nip between an ultrasonic welding horn and an anvil roll for conveying sheets.

The anvil roll is provided on its outer periphery with a seal pattern protruding section, and a welding portion is formed on each of the two sheets corresponding to the seal pattern protruding section. The seal pattern protruding section is provided with a groove formed corresponding to a portion where the elastically stretchable member is disposed. The groove has a depth that is set to cause a part of the elastically stretchable member to protrude from the groove when the elastically stretchable member is inserted into the groove.

Inserting a part of the elastically stretchable member into the groove reduces pressure for sandwiching the elastically stretchable member when the two sheets and the elastically stretchable member are ultrasonically welded while being sandwiched between the ultrasonic welding horn and the seal pattern protruding section of the anvil roll. This enables the two sheets and the elastically stretchable member to be welded without cutting the elastically stretchable member.

Thus, welding the elastically stretchable member to two sheets without cutting the elastically stretchable member requires the elastically stretchable member to be prevented from being detached from the groove of the seal pattern protruding section. For this reason, the apparatus described in Patent Literature 1 is provided with a guide member upstream of the anvil roll in a direction of supplying the elastically stretchable member to the anvil roll. The guide member is disposed away from an outer peripheral surface of the anvil roll, and guides the elastically stretchable member into the groove of the seal pattern protruding section on the anvil roll.

The apparatus of Patent Literature 1 is configured to guide the elastically stretchable member into the groove of the seal pattern protruding section on the anvil roll using the guide member, and the elastically stretchable member may be detached from the groove due to influence of vibration of the apparatus or the like. This requires to improve a function of preventing cutting by reducing a defect in which the elastically stretchable member is detached from the groove.

CITATION LIST

Patent Literature

Patent Literature 1: International Publication WO 2016/208502 A

SUMMARY OF INVENTION

It is an object of the present invention to provide a manufacturing apparatus for manufacturing a composite stretchable member capable of improving a function of preventing cutting by reducing a defect in which an elastic member is detached from a groove of a conveying roller.

To solve the problem above, a manufacturing apparatus for manufacturing a composite stretchable member according to the present invention is configured to bond two sheets to each other and bond the sheets to multiple elastic members while conveying each of the sheets in a longitudinal direction to manufacture a composite stretchable member including the two sheets, and the multiple elastic members sandwiched between the two sheets, the manufacturing apparatus for manufacturing a composite stretchable member including: a bonding device that welds and bonds the multiple elastic members to the two sheets, and the two sheets to each other, while the multiple elastic members are sandwiched between the two sheets being conveyed; and a guide device that guides the two sheets and the multiple elastic members to the bonding device in such a manner that each of the multiple elastic members extends in a longitudinal direction thereof and is sandwiched between the two sheets, the bonding device having: a conveying roller that has an outer peripheral surface used for conveying the two sheets sandwiching the multiple elastic members in the longitudinal direction of each of the two sheets and that rotates about an axis predetermined; and a compressing device that faces the outer peripheral surface of the conveying roller to compress the two sheets sandwiching the multiple elastic members between the outer peripheral surface of the conveying roller and the compressing device, the bonding device is configured to apply heat to the two sheets between the conveying roller and the compressing device, the outer peripheral surface of the conveying roller is provided with at least one protruding section formed protruding radially outward from the outer peripheral surface, the at least one protruding section includes multiple grooves extending in a conveying direction of the conveying roller and is away from each other in a direction parallel to the axis, the guide device having a guide member provided with a leading end closest to the outer peripheral surface of the conveying roller, the leading end being provided with the multiple guide grooves that hold the corresponding multiple elastic members, while being away from each other in a direction parallel to the axis of the conveying roller, to guide the multiple elastic members into the corresponding multiple grooves of the conveying roller, and the guide member being disposed to allow each of the multiple elastic members positioned between the guide grooves and the corresponding grooves of the conveying roller to have a length of 30 mm or less.

BRIEF DESCRIPTION OF DRAWINGS

FIG. 16 is a view schematically illustrating stages 1 to 3 for illustrating a method for manufacturing the disposable diaper illustrated in FIG. 15.

DESCRIPTION OF EMBODIMENTS

Hereinafter, embodiments of the present invention will be described with reference to the accompanying drawings. The following embodiments are merely examples embodying the present invention, and do not limit the technical scope of the present invention.

(1) Configuration of Composite Stretchable Member

Figure 1:
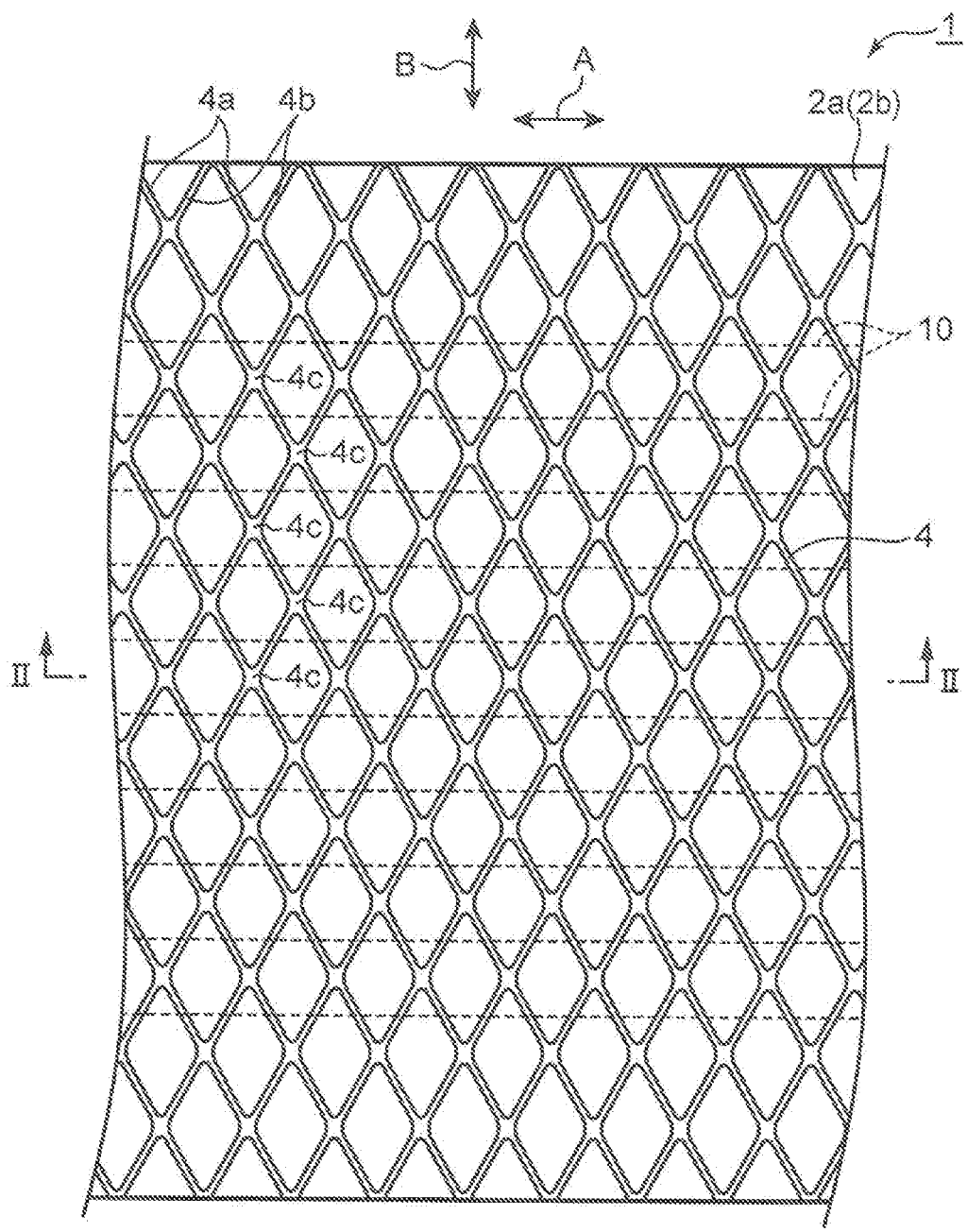
FIG. 1 is a plan view of a composite stretchable member manufactured by a manufacturing apparatus according to an embodiment of the present invention.
Figure 2:
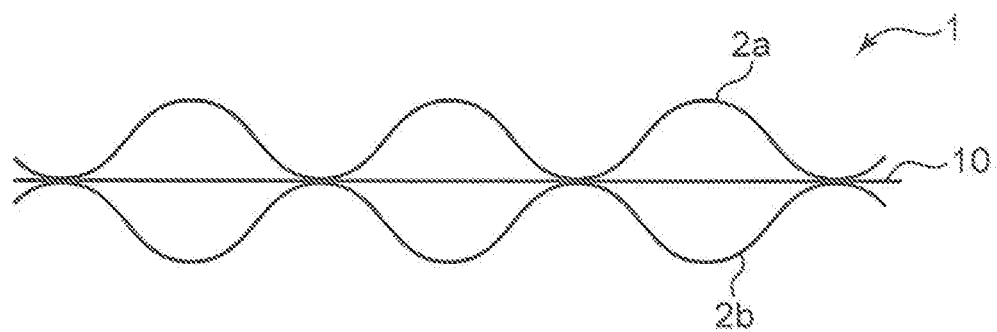
FIG. 2 is a part of a sectional view taken along line II-II in FIG. 1.

FIG. 1 is a plan view of a composite stretchable member manufactured by a manufacturing apparatus according to an embodiment of the present invention. FIG. 2 is a part of a sectional view taken along line II-II in FIG. 1.

A composite stretchable member 1 includes two elongated sheets 2a, 2b facing each other, and multiple elongated elastic members 10 stretchable in a longitudinal direction A. Each of the elastic members 10 is disposed between the sheets 2a, 2b so as to be stretchable in the longitudinal direction A (the left-right direction in FIG. 1) of each of the sheets 2a, 2b, i.e., so as to extend and contract in the longitudinal direction A of each of the sheets 2a, 2b along the longitudinal direction A. In the present embodiment, the elastic members 10 are disposed at equal intervals in a width direction B (a direction orthogonal to the longitudinal direction A of the sheets 2a, 2b) of the sheets 2a, 2b, and extend parallel to the longitudinal direction A of the sheets 2a, 2b.

In the present embodiment, a sheet-like material such as a nonwoven fabric is used as the sheets 2a, 2b.

Figure 3:
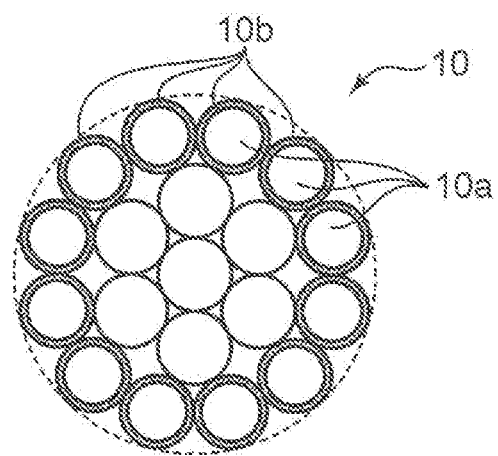
FIG. 3 is a schematic sectional view illustrating a section of an elastic member.

An elastic member 10 is made of a material that is more elastic than the material (nonwoven fabric or the like) of the sheets 2a, 2b, and the material of the elastic member 10 is not particularly limited in the present invention. As an example of the present embodiment is illustrated in FIG. 3, the elastic member 10 is a multi-strand provided with multiple rubber threads (fibrous elastic bodies) 10a collected in a bundle, and includes at least some of the rubber threads 10a each having the periphery covered with a covering layer 10b, for example. Specifically, the rubber threads 10a disposed particularly in an outer peripheral portion among the multiple rubber threads 10a are each covered with the covering layer 10b. Every rubber thread 10a may be covered with the covering layer 10b.

Examples of the material of the rubber thread 10a include polyurethane. Examples of the material of the covering layer 10b include a lubricant such as silicon oil or magnesium stearate.

FIG. 1 illustrates a bonding section 4 in a lattice shape on which the sheets 2a, 2b are bonded to each other, and the sheets 2a, 2b are bonded to the elastic members 10.

Figure 4:
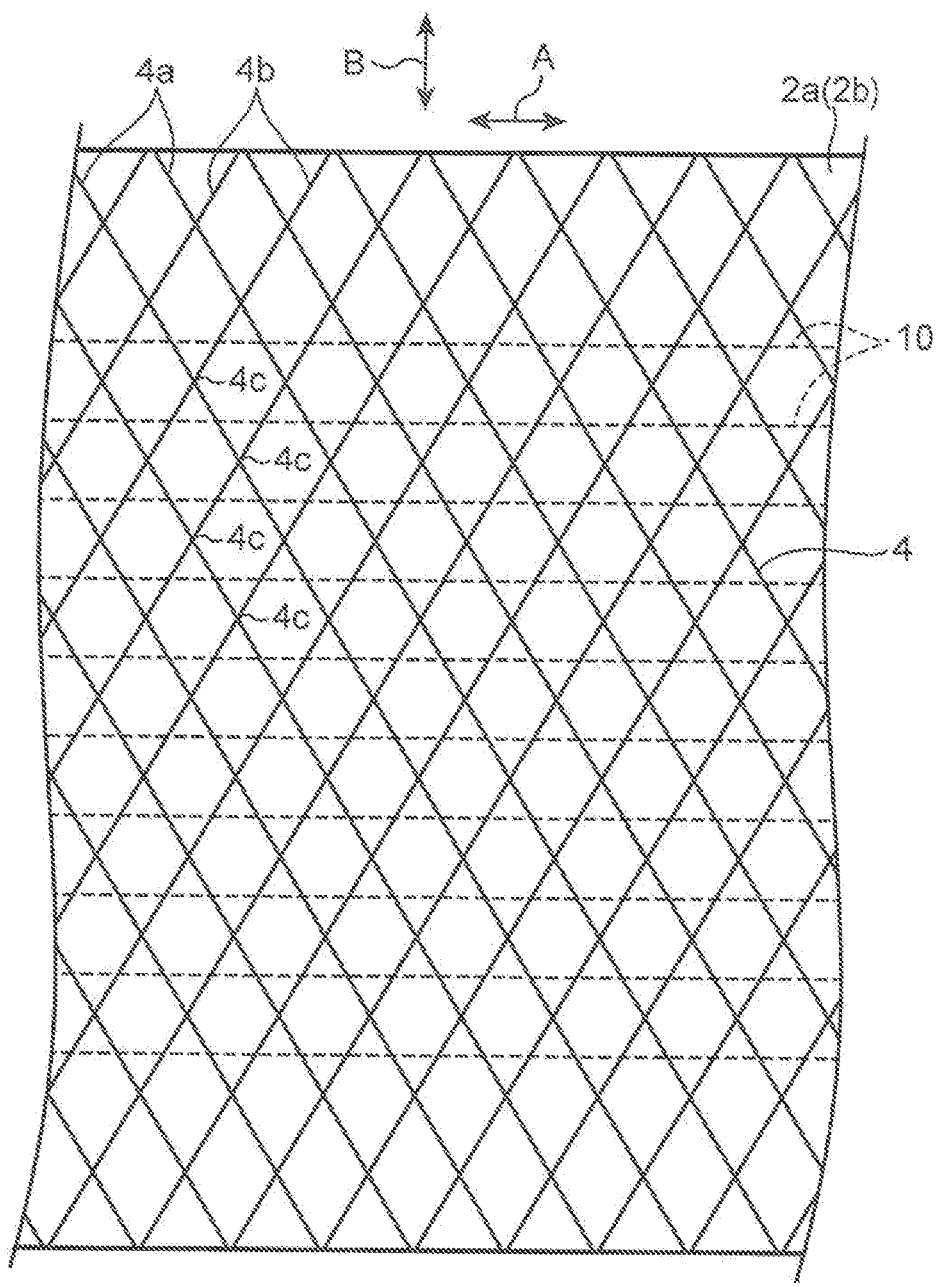
FIG. 4 is a view corresponding to FIG. 1 and schematically illustrating a bonding section.

FIG. 4 schematically illustrates the bonding section of FIG. 1. As illustrated in FIGS. 1 and 4, the bonding section 4 includes multiple first bonding portions 4a and multiple second bonding portions 4b.

The first bonding portions 4a are disposed at equal intervals in the longitudinal direction A of the sheets 2a, 2b, and extend parallel to each other in the width direction B of the sheets 2a, 2b.

The second bonding portions 4b are also disposed at equal intervals in the longitudinal direction A of the sheets 2a, 2b, and extend parallel to each other in the width direction B of the sheets 2a, 2b. The second bonding portions 4b extend intersecting the corresponding first bonding portions 4a, thereby forming the bonding section 4 in a lattice shape.

In the present embodiment, both a first bonding portion 4a and a second bonding portion 4b are inclined with respect to the width direction B of the sheets 2a, 2b. The inclination angle is smaller than 45 degrees. For example, the inclination angle is set to 30 degrees.

The first bonding portion 4a and the second bonding portion 4b each have a symmetrical shape with respect to both straight lines extending in the longitudinal direction A and the width direction B of the sheets 2a, 2b. The first bonding portions 4a and the second bonding portions 4b are disposed such that a clearance between two adjacent first bonding portions 4a is equal to a clearance between two adjacent second bonding portions 4b. This causes the bonding section 4 to have multiple defined rhombuses each having diagonals extend along the longitudinal direction A and the width direction B of the sheets 2a. 2b. As described above, the first bonding portion 4a and the second bonding portion 4b are each inclined with respect to the width direction B of the sheets 2a, 2b at an angle smaller than 45 degrees, and thus the first bonding portion 4a and the second bonding portion 4b form a rhombus extending in the width direction B. Intersections 4c between the first bonding portions 4a and the corresponding second bonding portions 4b, which may be referred to below as bonding-portion side intersections, are arranged at equal intervals on a straight line extending in the longitudinal direction A of the sheets 2*a*, 2*b*, and are arranged at equal intervals on a straight line extending in the width direction B of the sheets 2*a*, 2*b*.

Each bonding section 4 intersects all the elastic members 10 and extends along a line intersecting an extending direction (i.e., the longitudinal direction A) of the elastic members 10. Specifically, each bonding section 4 extends between opposite outer portions of the sheets 2*a*, 2*b* in the width direction B across a region where the elastic members 10 are disposed.

Each of the elastic members 10 and the bonding section 4 intersect at a portion excluding the bonding-portion side intersection 4*c*, i.e., at a position away from the bonding-portion side intersection 4*c*, and each of the elastic members 10 is bonded to the sheets 2*a*, 2*b* at this position.

Figure 5:
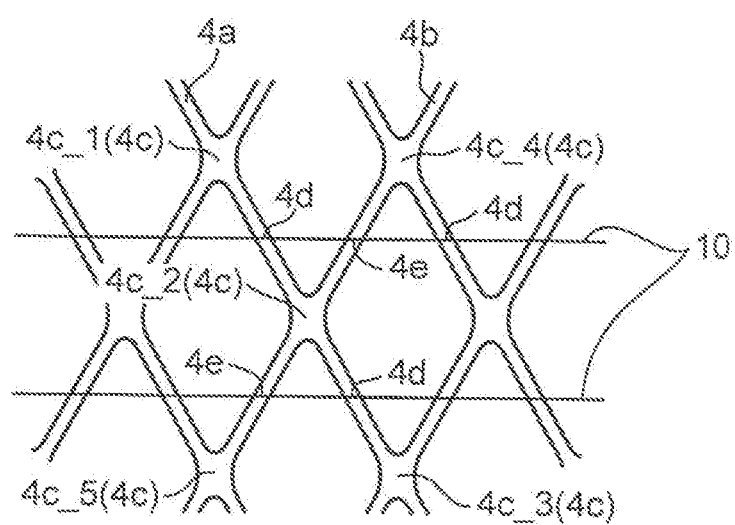
FIG. 5 is an enlarged view of a part of FIG. 1.

With reference to FIG. 5 that is an enlarged view of a part of FIG. 1, the configuration will be specifically described.

Each elastic member 10 is disposed passing through between two adjacent bonding-portion side intersections 4*c* on each first bonding portion 4*a* (e.g., between a bonding-portion side intersection 4*c*_1 and a bonding-portion side intersection 4*c*_2, and between a bonding-portion side intersection 4*c*_2 and a bonding-portion side intersection 4*c*_3 illustrated in FIG. 5). That is, a first elastic-member side intersection 4*d*, which is an intersection between each elastic member 10 and the corresponding one of the first bonding portions 4*a*, is positioned between two adjacent bonding-portion side intersections 4*c* on the first bonding portion 4*a*, and the elastic member 10 is bonded to the sheets 2*a*, 2*b* at this position 4*d*.

Similarly, each elastic member 10 is disposed passing through between adjacent bonding-portion side intersections 4*c* on each second bonding portion 4*b* (e.g., between a bonding-portion side intersection 4*c*_4 and a bonding-portion side intersection 4*c*_2, and between a bonding-portion side intersection 4*c*_2 and a bonding-portion side intersection 4*c*_5 illustrated in FIG. 5). That is, a second elastic-member side intersection 4*e*, which is an intersection between each elastic member 10 and the corresponding one of the second bonding portions 4*b*, is positioned between two adjacent bonding-portion side intersections 4*c* on the second bonding portion 4*b*, and the elastic member 10 is bonded to the sheets 2*a*, 2*b* at this position 4*e*.

In the present embodiment, each elastic member 10 passes through the center of the adjacent bonding-portion side intersections 4*c* and 4*c* on each first bonding portion 4*a*, and the center of the adjacent bonding-portion side intersections 4*c* and 4*c* on each second bonding portion 4*b*, and intersects the first bonding portion 4*a* and the second bonding portion 4*b* at the center position to be bonded to the sheets 2*a*, 2*b*.

This causes the first elastic-member side intersection 4*d* and the second elastic-member side intersection 4*e* to be alternately arranged on a straight line extending in the width direction B of both the sheets 2*a*, 2*b*. Intersections between the respective elastic members 10 and the bonding section 4, i.e., bonding points 4*d* and 4*e* between the elastic members 10 and the sheets 2*a*, 2*b* are disposed at equal intervals in the longitudinal direction A of the sheets 2*a*, 2*b*.

In the bonding section 4, the sheets 2*a*, 2*b* as well as the sheets 2*a*, 2*b* and the elastic member 10 are bonded to each other by welding. In the present embodiment, these are ultrasonically welded.

The sheets 2*a*, 2*b* are bonded to each other by being partially melted and welded. In contrast, the elastic member 10 and the sheets 2*a*, 2*b* are welded to each other when the sheets 2*a*, 2*b* are partially melted and the covering layer 10*b* of the elastic member 10 is melted.

Specifically, in the present embodiment, a rubber thread having a melting point of about 200° C. is used as the rubber thread 10*a*, and the covering layer 10*b* is made of magnesium stearate (melting point: about 120° C.) having a lower melting point than the rubber thread. When the elastic member 10 and the sheets 2*a*, 2*b* are welded to each other, the covering layer 10*b* is melted to weld the covering layer 10*b* to the sheets 2*a*, 2*b* without melting of the rubber thread 10*a*.

(2) Manufacturing Apparatus for Manufacturing a Composite Stretchable Member

Next, a manufacturing apparatus for manufacturing the composite stretchable member 1 will be described.

Figure 6:
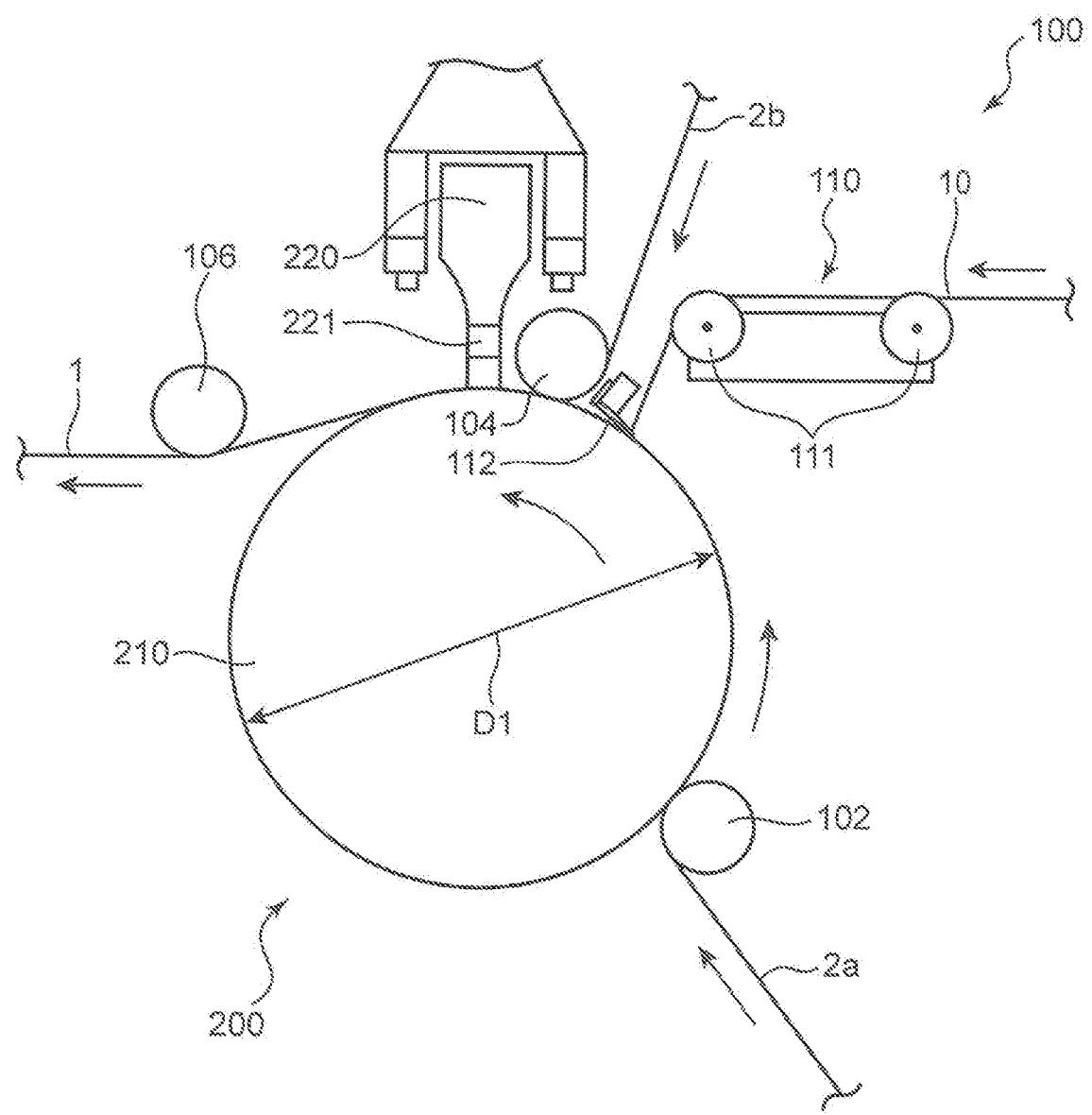
FIG. 6 is a schematic view illustrating a configuration of a manufacturing apparatus for manufacturing a composite stretchable member according to an embodiment of the present invention.
Figure 7:
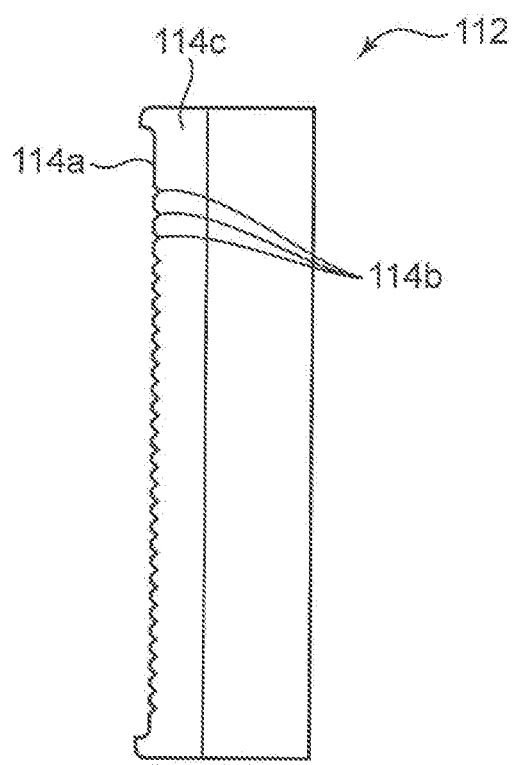
FIG. 7 is a plan view of the guide plate of FIG. 6.

FIG. 6 is a schematic view of a manufacturing apparatus 100 according to an embodiment of the present invention.

The manufacturing apparatus 100 includes: a bonding device 200 that ultrasonically welds and bonds the elastic member 10 to the sheets 2*a*, 2*b*, and the sheets 2*a*, 2*b* to each other while the elastic member 10 is sandwiched between the sheets 2*a*, 2*b*; a first guide roller 102 that guides the sheet 2*a* to the bonding device 200 (specifically, an anvil roll 210 described later); an elastic member guide device (guide device) 110 that supplies the elastic member 10 to the bonding device 200; a nip roll (second guide roller) 104 that guides the sheet 2*b* to the bonding device 200 and presses the two sheets 2*a*, 2*b*, and the elastic member 10; and a third guide roller 106 that guides a bonded sheet or the like, i.e., the composite stretchable member 1.

The bonding device 200 includes the anvil roll (conveying roller) 210 and a horn (compressing device) 220.

The anvil roll 210 is a rotating member that rotates about an axis extending in a direction orthogonal to the paper surface of FIG. 6. Hereinafter, the direction orthogonal to the paper surface of FIG. 6 is referred to as a "front-back direction". The anvil roll 210 is rotatably attached to a rotation shaft, as a rotation center, extending horizontally with respect to a vertical wall portion of an apparatus, such as a panel (not illustrated). The anvil roll 210 rotates to convey the elastic member 10 guided by the elastic member guide device 110 while the elastic member 10 is sandwiched between the sheets 2*a*, 2*b* guided by the rollers 102 and 104, respectively, on the outer peripheral surface of the anvil roll 210. In the example illustrated in FIG. 6, the anvil roll 210 rotates counterclockwise in FIG. 6. Hereinafter, the sheets 2*a*, 2*b* sandwiching the elastic member 10 may be referred to as pre-bonding sheets.

Figure 11:
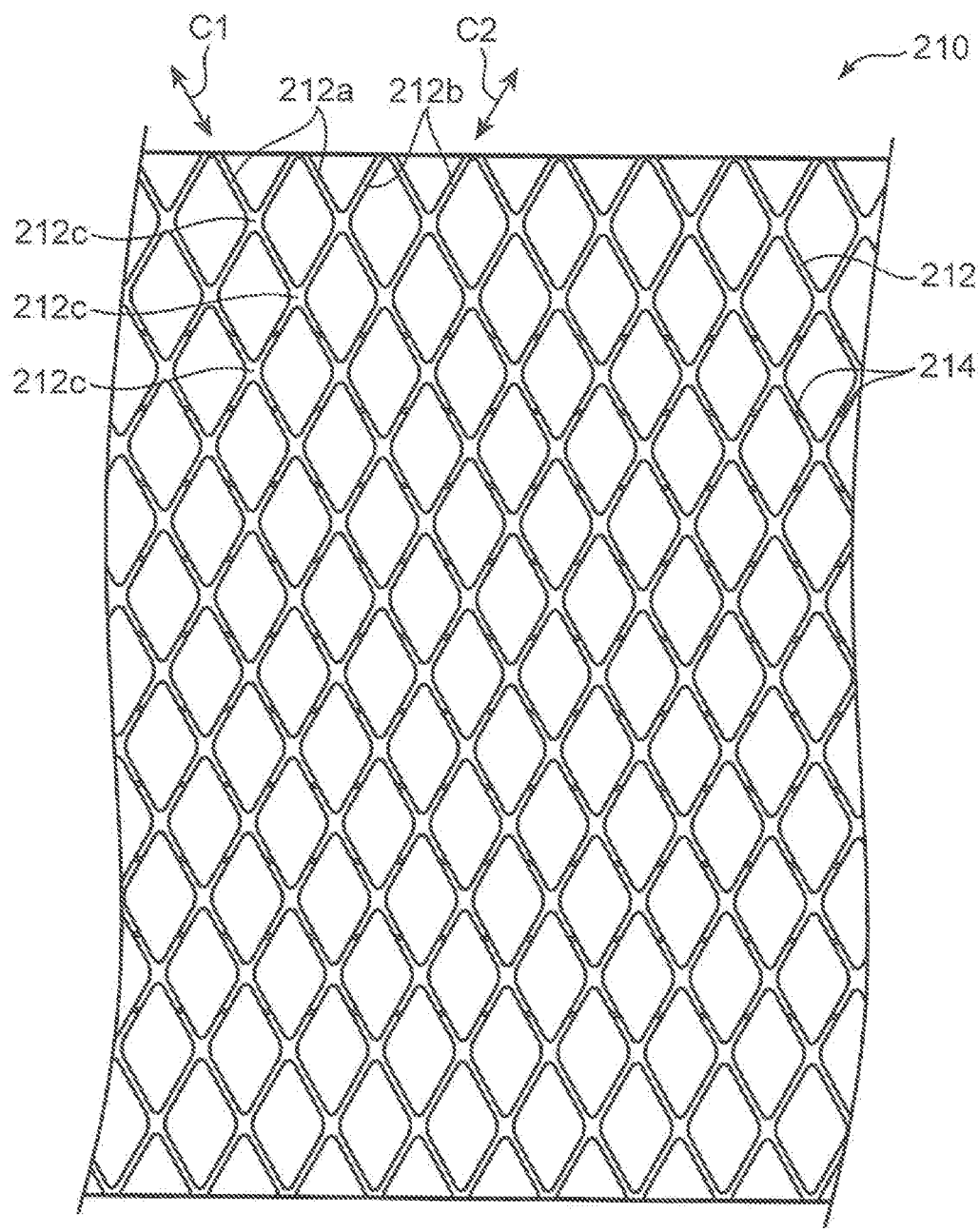
FIG. 11 is a view illustrating an outer peripheral surface of the anvil roll of FIG. 6.

As illustrated in FIG. 11, the outer peripheral surface of the anvil roll 210 is provided with a protruding section 212 protruding radially outward. The protruding section 212 is provided on the outer peripheral surface of the anvil roll 210 throughout the outer peripheral surface in its circumferential direction. The protruding section 212 has a shape corresponding to that of the bonding section 4. In the present embodiment, the bonding section 4 has a rhombic lattice shape as described above, and the protruding section 212 has a rhombic lattice shape correspondingly.

Specifically, the protruding section 212 includes first protruding portions 212*a* for forming the first bonding portions 4*a* and second protruding portions 212*b* for forming the second bonding portions 4*b*.

The first protruding portions 212*a* extend along a direction (first direction C1) intersecting the circumferential direction of the anvil roll 210 (conveying direction of the anvil roll 210), i.e., along a line intersecting the circumferential direction, and are disposed parallel to each other at equal intervals in the circumferential direction. The second protruding portions 212*b* extend along a direction (second direction C2) intersecting the circumferential direction of the anvil roll 210 and the first direction C1, i.e., along a line intersecting the circumferential direction, and are disposed parallel to each other at equal intervals in the circumferential direction of the anvil roll 210.

The first protruding portions 212a and the second protruding portions 212b are each symmetrically inclined at an angle smaller than 45 degrees with respect to the front-back direction, and are provided such that a clearance between two adjacent first protruding portions 212a is equal to a clearance between two adjacent second protruding portions 212b, and intersections 212c of the first protruding portions 212a and the corresponding second protruding portions 212b are arranged at equal intervals on a line extending in the front-back direction and the circumferential direction of the anvil roll 210.

Figure 12:
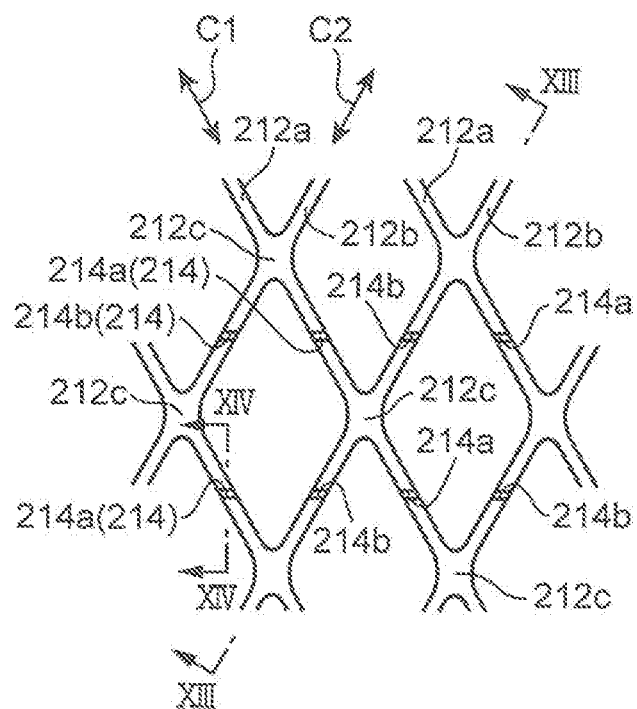
FIG. 12 is an enlarged view illustrating protruding sections and grooves on the outer peripheral surface of the anvil roll in FIG. 11.
Figure 13:
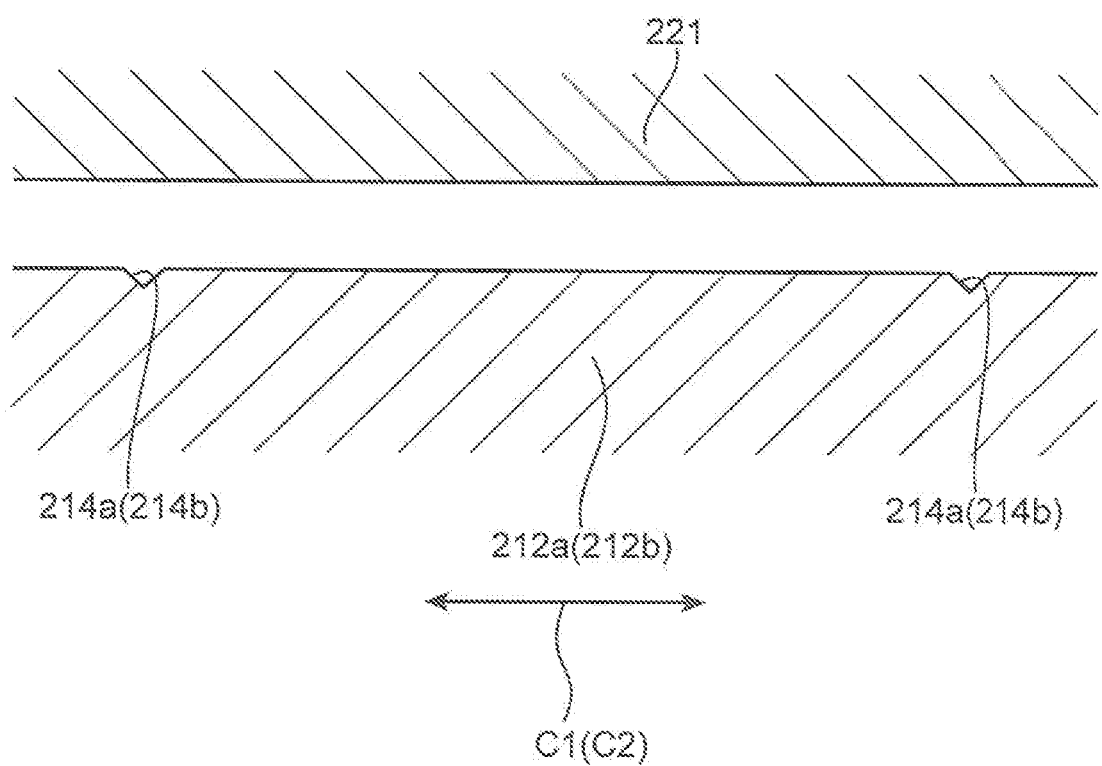
FIG. 13 is a sectional view taken along line XIII-XIII in FIG. 12.
Figure 14:
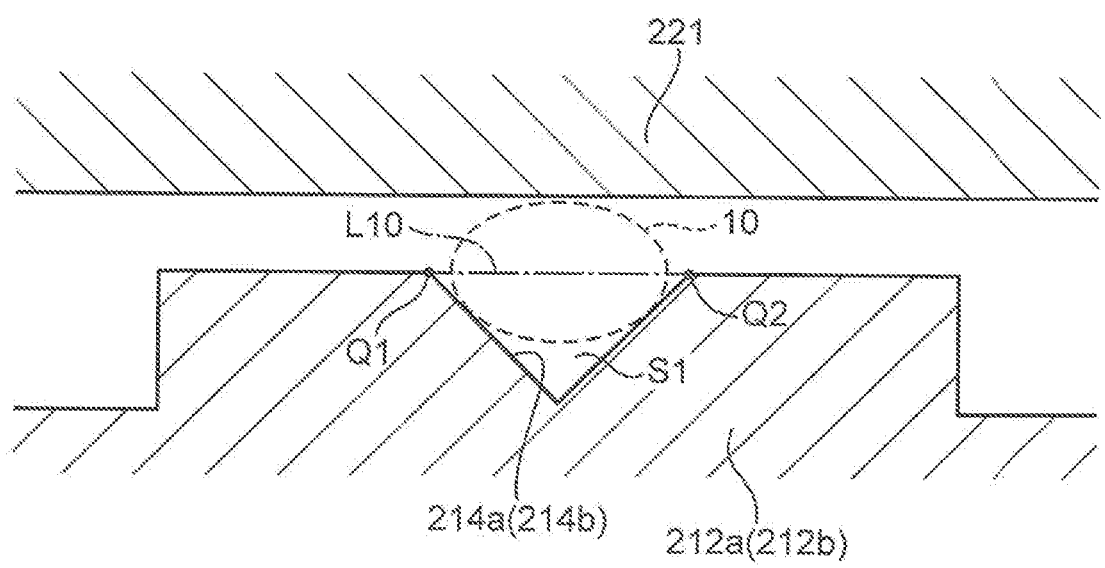
FIG. 14 is a sectional view taken along line XIV-XIV in FIG. 12.

As illustrated in FIG. 12 that is an enlarged view of a part of FIG. 11, FIG. 13 that is a sectional view taken along line XIII-XIII of FIG. 12, and FIG. 14 that is a sectional view taken along line XIV-XIV of FIG. 12, the first protruding portion 212a and the second protruding portion 212b are each provided with a groove 214 (214a or 214b) recessed inward in a radial direction of the anvil roll 210. As illustrated in FIG. 13 and the like, the first protruding portions 212a and the second protruding portions 212b are each provided with multiple grooves 214 at respective positions away from each other in the longitudinal directions C1 and C2 thereof.

Into these grooves 214, a portion of the sheet 2a (sheet disposed on the anvil roll 210) with the elastic member 10 disposed is inserted. Thus, placement of the elastic members 10 for the bonding section 4 coincides with placement of the grooves for the protruding section 212.

Specifically, in the present embodiment, as illustrated in FIG. 12, the first protruding portions 212a are each provided with the grooves (first grooves) 214a extending in the circumferential direction of the anvil roll 210, being each formed in a portion between intersections 212c with the corresponding second protruding portions 212b, more specifically, in a central portion of adjacent intersections 212c. The second protruding portions 212b are each provided with the grooves (second grooves) 214b that are each formed in a portion between intersections 212c with the corresponding first protruding portions 212a, more specifically, in a central portion of adjacent intersections 212c. These grooves 214 are provided at equal intervals on a line extending along the circumferential direction of the anvil roll 210, and are provided at equal intervals on a straight line extending along the front-back direction (i.e., a direction parallel to the rotation shaft of the anvil roll 210, in other words, the same direction as the extending direction of the rotation shaft).

The sheet 2a is conveyed by the anvil roll 210 while having a portion where the elastic member 10 is disposed, the portion being inserted into the corresponding grooves 214. As described above, in the present embodiment, the elastic members 10 are guided into the corresponding grooves 214 by a guide plate 112 provided with guide grooves 114b at positions corresponding to the respective grooves 214, so that the elastic members 10 are each stably disposed at an appropriate position on the sheet 2a.

In the present embodiment, the sheet 2a together with the elastic members 10 that are partially inserted into the corresponding grooves 214 are conveyed by the anvil roll 210. Only the sheet 2a with portions inserted into the grooves may be conveyed.

The grooves 214 are formed in the protruding section 212 at portions where the respective elastic members 10 are disposed as described above, so that at least a part of each of the elastic members 10 disposed on a pre-bonding sheet is retracted in the corresponding grooves when the pre-bonding sheet is compressed during bonding. Thus, an elastic member 10 is prevented from being cut when being compressed.

However, when the groove 214 has an excessive sectional area, the elastic member 10 may be less likely to be appropriately bonded to the sheets 2a, 2b. Thus, in the present embodiment, as illustrated in FIG. 14, when the elastic member 10 with a natural length is disposed in the groove 214, a part of the elastic member 10 protrudes outward from the groove 214, and the rest of the elastic member 10 is accommodated in the groove 214. Specifically, the groove 214 is configured to have a section taken along a plane orthogonal to the circumferential direction (conveying direction) of the anvil roll 210, the section having a shape in which when the elastic member 10 is disposed in the groove 214 with the natural length, a part of the elastic member 10 protrudes outward in the radial direction of the anvil roll 210 from a linear imaginary line L10 connecting open ends (Q1, Q2) of the groove 214. The groove 214 is also configured to have the sectional shape in which when the elastic member 10 is extended from a natural state (e.g., when being elongated 300%) is disposed in the groove 214, a part of the elastic member 10 protrudes outward in the radial direction of the anvil roll 210 from the linear imaginary line L10 connecting the open ends (Q1, Q2) of the groove 214. The groove 214 described above preferably has a sectional shape of a substantially V-shape as illustrated in FIG. 14. The groove 214 described above preferably has a sectional area SI smaller than a sectional area of the elastic member 10 to be disposed. The sectional shape of the groove 214 is not limited to a V-shape, and may be another shape such as a U-shape.

As described above, when the groove 214 is formed with a sectional shape allowing the elastic member 10 to partially protrude, the elastic member 10 disposed in the groove and the sheets 2a, 2b can be appropriately compressed and bonded to each other during ultrasonic welding while the elastic member 10 is retracted into the groove 214. Thus, the sheets 2a, 2b and the elastic members 10 can be more reliably bonded to each other while the elastic members 10 is prevented from being damaged. Specifically, a portion of the elastic member 10 inside the imaginary line L10, i.e., the portion accommodated in the groove 214, can be retracted inside the groove 214 (a side away from the horn 220) while pressure is appropriately applied to a portion of the elastic member 10, protruding outside the imaginary line L10 connecting the open ends Q1 and Q2 of the groove 214, and the sheets 2a, 2b. This enables preventing the elastic member 10 from being damaged while securing bonding force between the elastic member 10 and the sheets 2a, 2b.

In particular, when the sectional shape of the groove 214 is set such that the elastic member 10 partially protrudes outward in the radial direction of the anvil roll 210 from the linear imaginary line L10 connecting the open ends (Q1. Q2) of the groove 214 when the elastic member 10 elongated 300% is disposed in the groove 214, the sheets 2a, 2b and the elastic member 10 can be more reliably bonded to each other by being appropriately subjected to pressure while the elastic member 10 is prevented from being damaged.

Figure 10A:
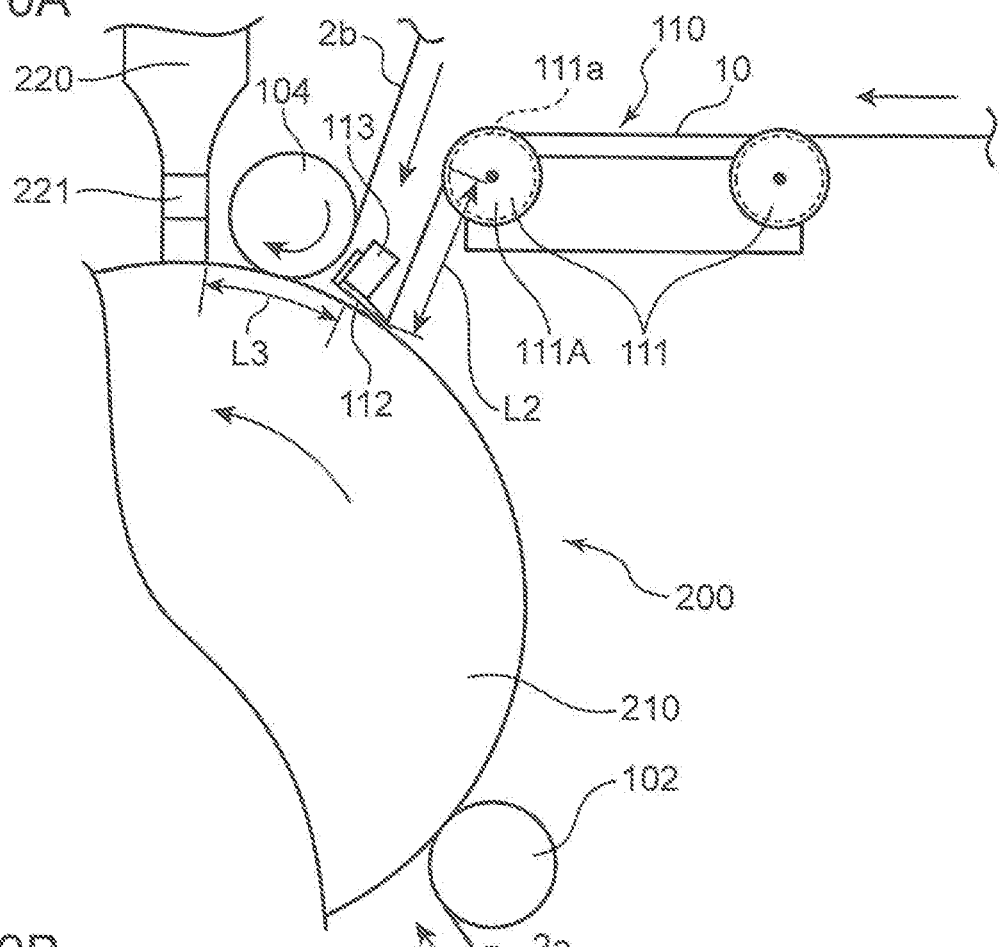
FIG. 10A is an enlarged view of the guide plate and a peripheral portion thereof of the manufacturing apparatus of FIG. 6.

The horn 220 illustrated in FIGS. 6 and 10A is a device that applies ultrasonic vibration to a pre-bonding sheet conveyed by the anvil roll 210 while compressing (pressurizing while sandwiching) the pre-bonding sheet with the outer peripheral surface of the anvil roll 210. The horn 220 is disposed to face the outer peripheral surface of the anvil roll 210. In the example of FIG. 6, the horn 220 is disposed to face an upper portion of the outer peripheral surface of the anvil roll 210. The horn 220 is provided at its leading end with an output unit 221 that applies ultrasonic vibration toward the outer peripheral surface of the anvil roll 210.

The horn 220 applies ultrasonic vibration to a pre-bonding sheet with the output unit 221 pressing against the pre-bonding sheet and compressing the pre-bonding sheet together with the anvil roll 210. This causes the sheets 2a, 2b to be melted and welded to each other. The elastic member 10 is also melted, so that the elastic member 10 and the sheets 2a. 2b are welded to each other. Specifically, the output unit 221 compresses the pre-bonding sheet together with the protruding section 212, and bonds the sheets 2a, 2b to each other and bonds the elastic member 10 to the sheets 2a, 2b in a portion of the pre-bonding sheet disposed on the protruding section 212. The leading end of the output unit 221 has a planar shape (See FIGS. 13 and 14).

As described above, in the present embodiment, the covering layer 10b is made of magnesium stearate having a lower melting point than the rubber thread 10a. Thus, during welding between the elastic member 10 and the sheets 2a, 2b, the covering layer 10b is melted to weld the covering layer 10b to the sheets 2a, 2b without melting of the rubber thread 10a.

The output unit 221 at the leading end of the horn 220 extends in the front-back direction, and the horn 220 applies ultrasonic vibration to the outer peripheral surface of the anvil roll 210 throughout in a rotation axis direction of the anvil roll 210. While a pre-bonding sheet is conveyed by the anvil roll 210, the horn 220 always applies ultrasonic vibration. Thus, as the pre-bonding sheet is conveyed by the anvil roll 210, the pre-bonding sheet is continuously bonded.

As illustrated in FIG. 6, in the present embodiment, the sheet 2a is guided by the first guide roller 102 to a position separated upstream from the horn 220 on the outer peripheral surface of the anvil roll 210. The sheet 2a is conveyed toward the horn 220 along the outer peripheral surface of the anvil roll 210 along with rotation of the anvil roll 210.

The sheet 2b is introduced into a portion of the outer peripheral surface of the anvil roll 210, being near the horn 220 and upstream of the horn 220 in the conveying direction, by the nip roll 104.

The elastic member 10 is introduced onto the outer peripheral surface of the anvil roll 210 at a position between a position where the sheet 2a is introduced onto the anvil roll 210 and a position where the sheet 2b is introduced onto the anvil roll 210 by the elastic member guide device 110. As a result, the elastic member 10 is conveyed to a position facing the horn 220 while being sandwiched between the sheets 2a, 2b.

Although the sheet 2b may be introduced onto the anvil roll 210 from the nip roll 104 at any position between a position where the elastic member 10 is introduced and a position facing the horn 220, the position is preferably on a side close to the position facing the horn 220, and more preferably near the position facing the horn 220. In the present embodiment, as illustrated in FIGS. 6 and 10A, the nip roll 104 is disposed at a position closest upstream of the horn 220 in the conveying direction of the sheets 2a, 2b. i.e., the rotation direction of the anvil roll 210 (counterclockwise direction in FIG. 10A). This configuration enables preventing the elastic member 10 introduced onto the outer peripheral surface of the anvil roll 210 from being covered with the sheet 2b at an early stage and from causing positional deviation.

The elastic members 10 are introduced onto the outer peripheral surface of the anvil roll 210 while being arranged parallel to each other in the front-back direction, and are placed on the sheet 2a, which is previously introduced onto the outer peripheral surface of the anvil roll 210, parallel to each other in the width direction B, on the outer peripheral surface of the anvil roll 210. The elastic members 10 are each introduced onto the anvil roll 210 while being elongated in the circumferential direction of the anvil roll 210. In the present embodiment, the elastic members 10 are each introduced onto the anvil roll 210 while being elongated 300% of the natural state when the natural state is set to 100%.

Next, the elastic member guide device 110 (in particular, the guide plate 112) of the present embodiment will be described in detail.

As illustrated in FIGS. 6 and 10, the elastic member guide device 110 includes multiple guide rolls 111 and a guide plate 112 in a plate-like shape as a guide member.

Each of the guide rolls 111 is a rotary member rotatable about its axis extending in the front-back direction, and guides the elastic member 10 toward the anvil roll 210 while the elastic member 10 is elongated (e.g., elongated 300%).

As illustrated in FIG. 6 to 10, the guide plate 112 is a tabular member that guides the elastic members 10 to the corresponding grooves 214 (see FIG. 11 to 14) formed on the outer peripheral surface of the anvil roll 210 while the elastic members 10 are separated from each other in the front-back direction, i.e., in a direction parallel to the axis of the anvil roll 210.

The guide plate 112 has a leading end 114a, which is an edge closest to the outer peripheral surface of the anvil roll 210, and a proximal end disposed farther away from the anvil roll 210 than the leading end 114a. The guide plate 112 is disposed to extend not only in a direction of coming into contact with and separating from the anvil roll 210 but also in the front-back direction. In the present embodiment, to prevent the guide plate 112 from interfering with the sheets 2a, 2b, the guide plate 112 has a thickness t (dimension in a vertical direction illustrated in FIG. 8) that is set to be small, and has a thin plate shape.

Figure 8:
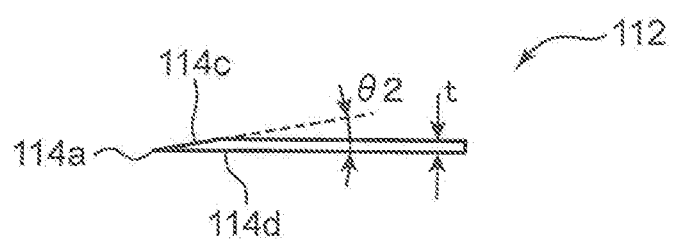
FIG. 8 is a side view of the guide plate of FIG. 7.

The leading end 114a of the guide plate 112 has a tapered shape. Specifically, as illustrated in FIG. 8, the guide plate 112 is provided in its leading end portion (portion close to the anvil roll 210) with an inclined surface 114c that is inclined toward the leading end 114a to approach a bottom surface 114d of the guide plate 112. The inclined surface 114e and the bottom surface 114d form the leading end 114a tapered. In the present embodiment, the inclined surface 114c and the bottom surface 114d form an angle θ2 that is set to about 10 degrees.

Figure 10B:
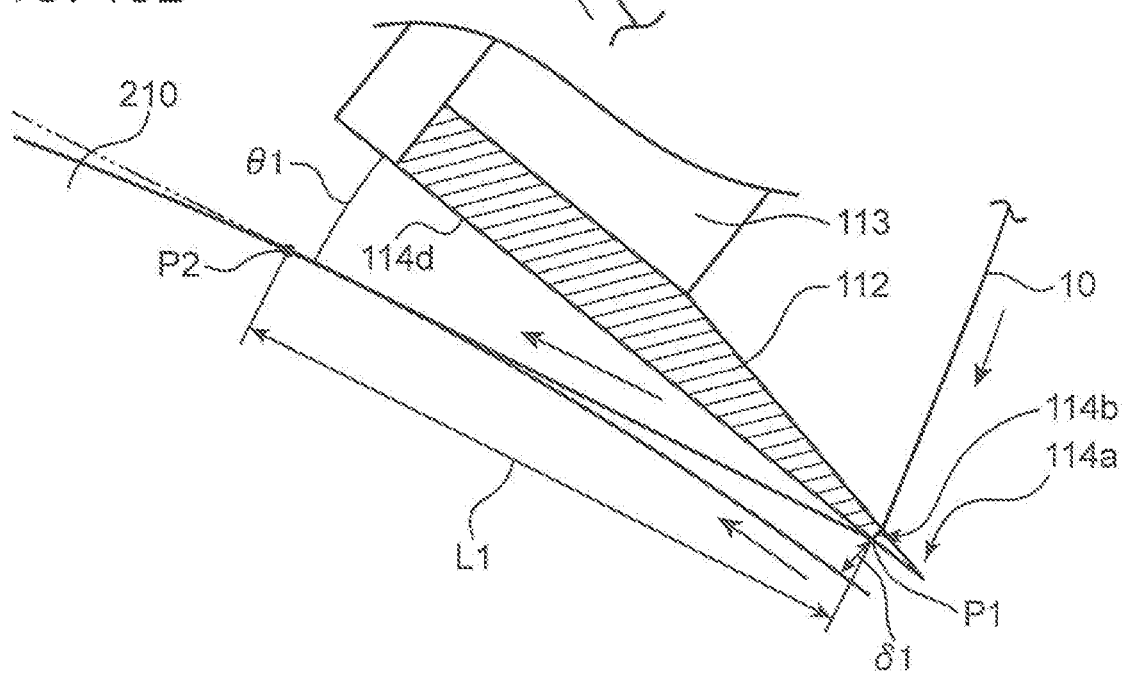
FIG. 10B is an enlarged view of a portion where an elastic member is fed from a guide groove of the guide plate of FIG. 10A to an anvil roll.

As illustrated in FIGS. 10A and 10B, the leading end 114a of the guide plate 112 is disposed upstream (right side in FIG. 10) of a contact point P2 at which the guide plate 112 is in contact with the elastic member 10 on the outer peripheral surface of the anvil roll 210 in the rotation direction (counterclockwise direction in FIG. 10) of the anvil roll 210 while facing upstream. The guide plate 112 is fixed in a stationary manner at a predetermined position facing the outer peripheral surface of the anvil roll 210. In FIGS. 10A and 10B, the guide plate 112 is fixed to a fixing member 113, which is fixed to a panel or the like inside the apparatus, by screwing or the like to be prevented from being displaced.

Figure 9:
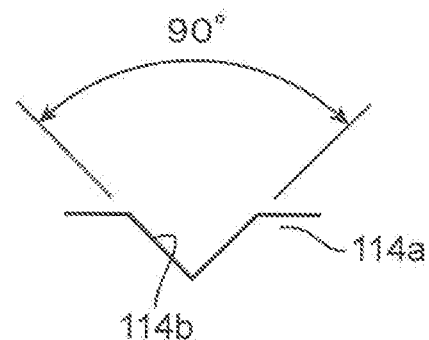
FIG. 9 is an enlarged view of a guide groove of the guide plate of FIG. 7.

The leading end 114a tapered of the guide plate 112 is provided with multiple guide grooves 114b. Specifically, the guide grooves 114b are formed at respective positions away from each other at equal intervals in the front-back direction (direction parallel to the axis of the anvil roll 210) at the leading end 114a of the guide plate 112, and individually hold the respective elastic members 10 to guide the elastic members 10 into the respective grooves 214 of the anvil roll 210. As illustrated in FIG. 9 that illustrates a part of the guide grooves 114b in FIG. 7 in an enlarged manner, each of the guide grooves 114b is recessed from the leading end 114a of the inclined surface 114c toward the proximal end, and has a V-shape having an opening angle of 90 degrees. The guide grooves 114b each have a sectional shape that is not limited to the V-shape, and that may be another shape such as a U-shape. These guide grooves 114b reliably position and hold the respective elastic members 10 to guide the elastic members 10 onto the outer peripheral surface of the anvil roll 210 while separating the elastic members 10 from each other in the front-back direction. The guide grooves 114b face the respective grooves 214 formed in the anvil roll 210 and are provided at the same intervals as the grooves 214 to guide the elastic members 10 into the respective grooves 214.

The leading end 114a of the guide plate 112 and the guide grooves 114b formed at the leading end 114a face in an opposite direction (i.e., a clockwise direction) to the rotation direction of the anvil roll 210 (the counterclockwise direction in FIGS. 6 and 10A). Thus, the elastic members 10 engaged into the respective guide grooves 114b are pulled by the anvil roll 210 rotating in the counterclockwise direction, and are bent at bottoms P1 of the respective guide groove 114b. Each of the elastic members 10 then extends in a tangential direction of the contact P2 on the outer peripheral surface of the anvil roll 210, and is inserted into the corresponding one of the grooves 214 (see FIG. 11 to 14) at the contact P2 on the outer peripheral surface of the anvil roll 210.

As illustrated in FIGS. 10A and 10B, it is conceivable that as a length L1 (specifically, a distance L1 from the bottom P1 of a guide groove 114b to the contact point P2 at which an elastic member 10 is in contact with the anvil roll 210) of the elastic member 10 positioned between the guide groove 114b and a groove 214 of the anvil roll 210 decreases in the guide plate 112, the elastic member 10 tends to be less likely to be detached from the groove 214 of the anvil roll 210.

As a result of experimentally examining a correlation between the length L1 (i.e., a free distance L1 with which the elastic member 10 moves in the air without being restrained) of the elastic member 10 positioned between the guide groove 114b and the groove 214 of the anvil roll 210 and probability of vibration of the elastic member 10, the present inventors have found that there is a correlation as shown in Table 1 below. In the experiment, a linear rubber thread having a diameter of 0.1 mm or more was used as the elastic member 10, and a frequency of touches of the rubber thread and the amount of vibration of the rubber thread were observed for a certain period of time by continuously inserting the rubber thread from the guide groove 114b of the guide plate 112 into the groove 214 of the anvil roll 210 in the manufacturing apparatus 100. Results of the experiment are shown in Table 1 below.

TABLE 1

| | FREE DISTANCE L1 | | |
|---|---|---|---|
| | 15 mm OR LESS | 15~30 mm OR LESS | 30~50 mm OR LESS |
| VIBRATION SUPPRESSION EFFECT OF ELASTIC MEMBER (RUBBER THREAD) | ◎ | Δ | X |
| PROBABILITY OF VIBRATION OF RUBBER THREAD WITH DIAMETER OF 0.1 mm OR MORE | 0.08% | 4.66% | 10% OR MORE |

The experimental results in Table 1 show that when the free distance L1 of the rubber thread is 15 mm or less, the rubber thread having a diameter of 0.1 mm or more has a probability of vibration of 0.08%, resulting in good (double circle) in vibration suppression effect of the rubber thread.

Even when having a free distance L1 of 15 mm to 30 mm or less in the range larger than 15 mm, the rubber thread has a probability of vibration of 4.66% that falls within the allowable probability (5%), and thus it can be seen that the vibration suppression effect of the rubber thread is a pass or a pass mark (triangle).

When having a free distance L1 within a range of more than 30 mm, e.g., 30 mm to 50 mm or less, the rubber thread has a probability of vibration of 10% or more that greatly exceeds the allowable probability (5%), and thus it can be seen that the vibration suppression effect of the rubber thread is unacceptable (cross).

To reduce a defect in which the elastic member 10 such as a rubber thread is detached from the groove 214 of the anvil roll 210 based on the above experimental results, the guide plate 112 of the present embodiment is preferably disposed such that the elastic member 10 positioned between the guide groove 114b and the groove 214 of the anvil roll 210 has a length L1 of 30 mm or less, preferably of 15 mm or less, and practically within a range of 1 mm to 30 mm, preferably within a range of 1 mm to 15 mm. The distance L1 is set to be larger than zero to prevent the guide plate 112 from coming into contact with the anvil roll 210 (specifically, the sheet 2a wound around the outer peripheral surface of the anvil roll 210), i.e., to allow the guide plate 112 to be separated by a thickness of the sheet 2a or more.

As illustrated in FIG. 10B, the guide plate 112 is disposed such that a gap 81 between the bottom P1 of the guide groove 114b and the outer peripheral surface of the protruding section 212 of the anvil roll 210 is 1 mm or less, preferably is 0.3 mm or less, and practically within a range of 0.1 mm to 1 mm, preferably within a range of 0.1 mm to 0.3 mm.

As illustrated in FIG. 10B, the guide plate 112 is disposed such that the bottom surface 114d facing the anvil roll 210 forms an angle θ1 of 30 degrees or less (practically, an angle within a range of 1 to 30 degrees) with respect to a tangent line of the anvil roll 210 at the contact point P2 where the anvil roll 210 and the elastic member 10 are in contact with each other.

As illustrated in FIGS. 6 and 10A, the multiple guide rolls 111 is disposed upstream of the guide plate 112 in the conveying direction of the elastic member 10, and guides the elastic member 10 into the guide groove 114b. Each of the guide rolls 111 is provided in its outer peripheral surface with grooves (not illustrated) away from each other in an extending direction of a rotation shaft of the guide roll 111 to guide the elastic members 10 into the respective guide grooves 114b.

As illustrated in FIG. 10A, a guide roll 111A positioned most downstream of the multiple guide rolls 111 is disposed to have a distance L2 of 50 mm or more in which the elastic member 10 is separated from the guide roll from the guide roll 111 and inserted into the guide groove 114b to prevent influence due to rotation unevenness and rattling of the guide roll 111A (e.g., a slack of the elastic member 10 and the like).

As illustrated in FIGS. 6 and 10A, the nip roll 104 is disposed upstream of the horn 220. The nip roll 104 can sandwich two sheets and the elastic member 10 in cooperation with the anvil roll 210 in a region where the elastic member 10 is inserted into the groove 214 of the anvil roll 210, i.e., a section from a first position (i.e., a contact point between the anvil roll 210 and the elastic member 10) P2 (see FIG. 10B) where the elastic member 10 is inserted into the groove 214 in the outer peripheral surface of the anvil roll 210 to the output unit 221 (see FIG. 10A) of the horn 220.

As illustrated in FIG. 10A, in the present embodiment, a conveying distance L3, in which the elastic member is compressed by the horn 220 after coming into contact with the groove 214 of the anvil roll 210, is set to 150 mm or less (practically, a range of 1 mm to 150 mm) to reduce a defect in which the elastic member 10 is detached from the groove 214 of the anvil roll 210 while the elastic member 10 is compressed by the horn 220 after coming into contact with the groove 214 of the anvil roll 210.

The conveying distance L3 described above has an optimum numerical value derived from experiments performed by the present inventors. Specifically, as shown in Table 2 below, when a linear rubber thread having a diameter of 0.1 mm or more was used as the elastic member 10, a relationship between the conveying distance L3, in which the rubber thread is compressed by the horn 220 after coming into contact with the groove 214 of the anvil roll 210, and the probability of vibration of the rubber thread, was examined through experiments.

TABLE 2

| CONVEYING DISTANCE L3 | FREE DISTANCE L1 = 11 mm | FREE DISTANCE L1 = 19 mm |
| --- | --- | --- |
| 20 mm | 0.08% | 1.12% |
| 150 mm | 0.16% | 3.66% |
| 300 mm | 5.73% | 9.62% |

The experimental results in Table 2 show that when the conveying distance L3 of the rubber thread is 150 mm, the probability of vibration of the rubber thread under conditions where the free distance L1 is 11 mm is 0.16%, and the probability of vibration of the rubber thread under conditions where the free distance L1 is 19 mm is 3.66%, which fall within an allowable probability (5%), and thus the vibration suppression effect of the rubber thread is sufficiently exhibited (passed). Table 2 also shows that when the conveying distance L3 is 20 mm, the probability of vibration of the rubber thread under the conditions where the free distance L1 is 11 mm decreases to 0.08%, and the probability of vibration of the rubber thread under the conditions where the free distance L1 is 19 mm decreases to 1.12%.

In contrast, when the conveying distance L3 of the rubber thread is 300 mm, the probability of vibration of the rubber thread under the conditions where the free distance L1 is 11 mm is 5.73%, and the probability of vibration of the rubber thread under the conditions where the free distance L1 is 19 mm is 9.62%, which greatly exceeds the allowable probability (5%), and thus the vibration suppression effect of the rubber thread is insufficient (failed).

The experimental results in Table 2 above show that the conveying distance L3 is preferably set to 150 mm or less to reduce a defect in which the elastic member 10 is detached from the groove 214 of the anvil roll 210 while the elastic member 10 is compressed by the horn 220 after coming into contact with the groove 214 of the anvil roll 210.

(3) Wearing Article and Method for Manufacturing the Same

Figure 15:
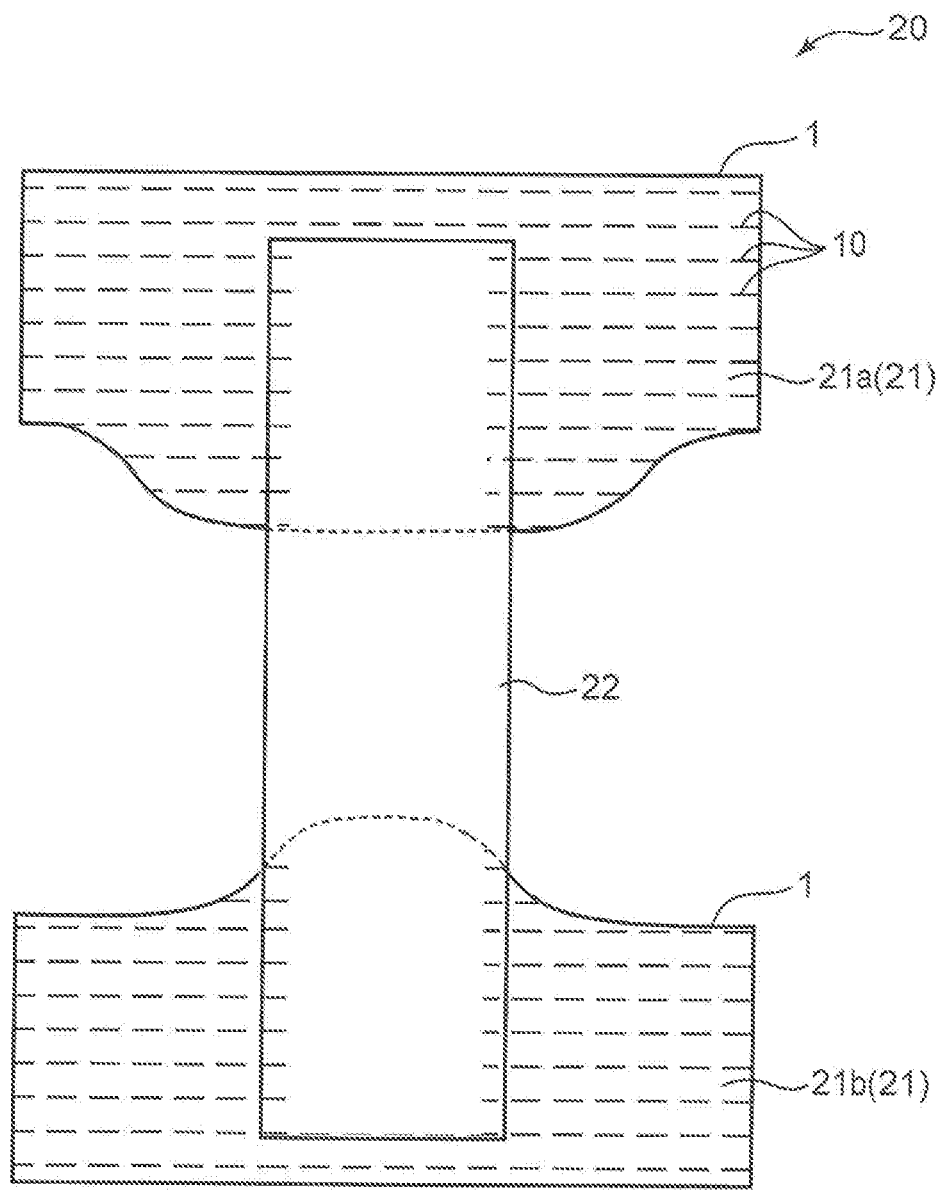
FIG. 15 is a developed view of a disposable diaper using a composite stretchable member.

FIG. 15 is a schematic view illustrating a disposable diaper (wearing article) 20 using the composite stretchable member 1 as a usage example of the composite stretchable member 1 configured as described above.

The disposable diaper 20 includes a waistline portion 21 having a front abdomen portion 21a disposed on the front of the abdomen of a wearer and a rear back portion 21b disposed on the buttocks of the wearer, and a crotch portion 22 disposed at the crotch of the wearer. The composite stretchable member 1 of the present embodiment is used for the front abdomen portion 21a and the rear back portion 21b. For example, the composite stretchable member 1 is applied to the front abdomen portion 21a and the rear back portion 21b such that the extending direction of the composite stretchable member 1 aligns with a waistline direction (left-right direction in FIG. 15) at the time of wearing.

FIG. 16 is a view illustrating an example of a method for manufacturing the disposable diaper 20, and the present invention is not limited thereto. The manufacturing method illustrated in FIG. 16 includes stages 1 to 3. First, in the stage 1, a pair of continuous bodies 101 in which composite stretchable members 1 are connected in the conveying direction is prepared. That is, a continuous body 101 for forming the front abdomen portion 21a and a continuous body 101 for forming the rear back portion 21b are prepared. Then, both the continuous bodies 101 are conveyed in the longitudinal direction of the continuous bodies 101 while being disposed parallel to each other, and the crotch portion 22 is placed on the continuous bodies 101 such that the longitudinal direction of the crotch portion is orthogonal to the longitudinal direction of the continuous bodies 101. For example, crotch portions 22 are placed away from each other in the conveying direction. Then, the crotch portions 22 are bonded the continuous bodies 101 to form a bonded body 103 (step of forming a bonded body).

Next, in the stage 2, a hole serving as a leg opening is formed between the crotch portions 22 adjacent to each other. After that, the bonded body 103 is folded in two along a center line CL1 in the width direction (direction orthogonal to the longitudinal direction of the continuous bodies 101) as a fold such that the crotch portion 22 is positioned inside (step of folding in two).

Next, in the stage 3, portions of the respective continuous bodies 101 positioned in the middle of the adjacent crotch portions 22, which overlap each other, are bonded to each other along a direction orthogonal to the longitudinal direction of the continuous bodies 101 to form a side seal SS (step of sealing a side), and the continuous bodies 101 are cut along a cutting line K in the side seal portion (step of cutting).

In this manner, the disposable diaper 20 including the waistline portion 21 (the front abdomen portion 21a and the rear back portion 21b) that is formed of the composite stretchable member 1 to stretch and contract in the waistline direction is manufactured.

In the present embodiment, the step of opening the hole serving as the leg opening may or may not be performed before the crotch portions 22 are bonded to the continuous bodies 101. Additionally, each elastic member 10 of the composite stretchable member 1 may be bonded to two sheets 2a, 2b with a hot melt adhesive near a portion corresponding to the cutting line K. In this way, coming off of each elastic member 10 due to cutting along the cutting line K can be prevented.

Features of the Present Embodiment (1)

The manufacturing apparatus 100 for manufacturing a composite stretchable member of the present embodiment is configured such that as illustrated in FIG. 6 to 10, the elastic member guide device 110 includes the guide plate 112 in a plate-like shape as a guide member that guides elastic members 10 to the respective grooves 214 in the outer peripheral surface of the anvil roll 210. The guide plate 112 includes the leading end 114a closest to the outer peripheral surface of the anvil roll 210, and the guide grooves 114b provided at the leading end 114a and holding the respective elastic members 10 in a state away from each other in a direction parallel to the axis of the anvil roll 210 to guide the elastic members 10 to the respective grooves 214 in the outer peripheral surface of the anvil roll 210 in the state away from each other in the direction parallel to the axis of the anvil roll 210. The guide plate 112 is disposed to allow the elastic member 10 positioned between the guide groove 114b and the groove 214 of the anvil roll 210 to have a length L1 (free distance L) of 30 mm or less.

As described above, disposing the guide plate 112 to allow the elastic member 10 positioned between the guide groove 114b and the groove 214 of the anvil roll 210 to have the length L1 of 30 mm or less enables reducing a defect in which the elastic member 10 is detached from the groove 214 of the anvil roll 210 when the elastic member 10 is fed from the guide groove 114b to the groove 214 of the anvil roll 210. As a result, a function of preventing cutting of the elastic member 10 can be improved.

(2)

The guide plate 112 is preferably disposed to allow the elastic member 10 positioned between the guide groove 114b and the groove 214 of the anvil roll 210 to have a length L1 of 15 mm or less. This case enables further reducing the defect in which the elastic member 10 is detached from the groove 214 of the anvil roll 210 when the elastic member 10 is fed from the guide groove 114b to the groove 214 of the anvil roll 210. As a result, the function of preventing cutting of the elastic member 10 can be further improved.

(3)

The manufacturing apparatus 100 for manufacturing a composite stretchable member according to the present embodiment is configured such that the guide plate 112 is disposed to allow the gap 81 between the bottom P1 of the guide groove 114b and the outer peripheral surface of the protruding section 212 of the anvil roll 210 to be 1 mm or less, preferably 0.3 mm or less. This configuration enables the guide groove 114b to approach the outer peripheral surface of the protruding section of the anvil roll 210, so that the distance L1, in which the elastic member 10 leaves the guide groove 114b and is inserted into the groove 214 of the anvil roll 210, can be shortened. This enables further reducing the defect in which the elastic member 10 is detached from the groove 214 of the anvil roll 210. As a result, the function of preventing cutting of the elastic member 10 can be further improved.

(4)

The manufacturing apparatus 100 for manufacturing a composite stretchable member of the present embodiment includes a guide member that guides the elastic members 10 onto the outer peripheral surface of the anvil roll 210 in a state where the elastic members 10 are away from each other in a direction parallel to the axis of the anvil roll 210, and that is formed of the guide plate 112 in a plate-like shape. The leading end 114a of the guide plate 112 is an edge of the guide plate 112 closest to the outer peripheral surface of the anvil roll 210 and has a tapered shape. The multiple guide grooves 114b is formed at the leading end 114a tapered. This configuration enables the guide plate 112 to be disposed close to the outer peripheral surface of the anvil roll 210 without interfering with the anvil roll 210 and the sheets 2a, 2b wound around the outer peripheral surface of the anvil roll 210, by using the guide plate 112 in a plate-like shape with the leading end 114a tapered. This enables further reducing the defect in which the elastic member 10 is detached from the groove 214 of the anvil roll 210, by shortening the distance L1 between the guide groove 114b and the groove 214 of the anvil roll 210. The guide groove 114b is formed at the leading end 114a tapered, so that frictional resistance between the elastic member 10 and the guide plate 112 when the elastic member 10 posses through the guide groove 114b can be reduced. As a result, the function of preventing cutting of the elastic member 10 can be further improved.

(5)

The manufacturing apparatus 100 for manufacturing a composite stretchable member of the present embodiment is configured such that the leading end 114a of the guide plate 112 is disposed upstream (right side in FIG. 10) of the contact point P2 at which the guide plate 112 is in contact with the elastic member 10 on the outer peripheral surface of the anvil roll 210 in the rotation direction (counterclockwise direction in FIG. 10) of the anvil roll 210 while facing upstream. The guide plate 112 is disposed such that the bottom surface 114d facing the anvil roll 210 forms an angle θ1 of 30 degrees or less with respect to the tangent line of the anvil roll 210 at the contact point P2 where the anvil roll 210 and the elastic member 10 are in contact with each other.

This configuration enables the bottom of the guide groove 114b to approach the outer peripheral surface of the anvil roll 210, so that the distance L1, in which the elastic member 10 leaves the guide groove 114b and is inserted into the groove 214 of the anvil roll 210, can be shortened. This enables further reducing the defect in which the elastic member 10 is detached from the groove 214 of the anvil roll 210. As a result, the function of preventing cutting of the elastic member 10 can be further improved.

(6)

The manufacturing apparatus 100 for manufacturing a composite stretchable member of the present embodiment further includes the nip roll 104 that is disposed on upstream of the horn 220 in the conveying direction of the sheets 2a, 2b (the rotation direction of the anvil roll 210) and sandwiches two sheets and the elastic member 10 in cooperation with the anvil roll 210 in the region where the elastic member 10 is inserted into the groove 214 of the anvil roll 210, i.e., the section from the contact point P2 (see FIG. 10B) that is the first position where the elastic member 10 is inserted into the groove 214 in the outer peripheral surface of the anvil roll 210 to the output unit 221 (see FIG. 10A) of the horn 220.

This configuration enables further reducing a defect in which the elastic member 10 inserted into the groove 214 of the anvil roll 210 is detached from the groove 214 of the anvil roll 210 before reaching the horn 220. As a result, the function of preventing cutting of the elastic member 10 can be further improved. Additionally, even when the elastic member 10 contracts and tries to return when the elastic member 10 is cut downstream of the nip roll 104, return of the elastic member 10 is prevented because an end portion of the elastic member 10 is sandwiched between the nip roll 104 and the anvil roll 210. This facilitates restoration work of the manufacturing apparatus 100.

(7)

The manufacturing apparatus 100 for manufacturing a composite stretchable member of the present embodiment is configured such that the elastic member guide device 110 further includes the guide roll 111 that is disposed upstream of the guide plate 112 in the conveying direction of the elastic member 10 to guide the elastic member 10 into the guide groove 114b. This configuration enables the elastic member 10 to be reliably guided into the guide groove 114b, so that the defect in which the elastic member 10 is detached from the guide groove 114b can be prevented.

(8)

The manufacturing apparatus 100 for manufacturing a composite stretchable member according to the present embodiment is configured such that the guide roll 111 (specifically, the guide roll 111A positioned most downstream of the multiple guide rolls 111) is disposed to allow the distance L2 in which the elastic member 10 is separated from the guide roll 11l and inserted into the guide groove 114b to be 50 mm or more. This configuration enables eliminating influence on the elastic member 10 due to rotation unevenness and rattling of the guide roll 111, such as a slack of the elastic member 10.

(9)

The manufacturing apparatus 100 for manufacturing a composite stretchable member of the present embodiment is configured such that the conveying distance L3, in which the elastic member 10 is compressed by the horn 220 after coming into contact with the groove 214 of the anvil roll 210, is 150 mm or less. This configuration allows the vibration suppression effect of the elastic member 10 to be sufficiently exerted as shown in Table 2 above, and thus enables reducing the defect in which the elastic member 10 is detached from the groove 214 of the anvil roll 210 during a period from when the elastic member 10 comes into contact with the groove 214 of the anvil roll 210 to when the elastic member 10 is compressed by the horn 220. As a result, the function of preventing cutting of the elastic member 10 can be further improved.

(Modification)

(A)

Although in the present embodiment, the guide plate 112 in a plate-like shape has been described as an example of the guide member that guides the elastic members 10 onto the outer peripheral surface of the anvil roll 210 while the elastic members 10 are separated from each other in the direction parallel to the axis of the anvil roll 210, the present invention is not limited thereto.

As a modification of the present invention, instead of the guide plate 112 in a plate-like shape, a guide roller or the like having multiple guide grooves in its outer peripheral surface may be used as another guide member. Even the guide roller enables the elastic members 10 to be guided into the respective grooves 214 in the outer peripheral surface of the anvil roll 210 while the elastic members 10 are separated from each other in the direction parallel to the axis of the anvil roll 210.

Even this configuration enables reducing the defect in which the elastic member 10 is detached from the groove 214 of the anvil roll 210 when the elastic member 10 is fed from the guide groove to the groove 214 of the anvil roll 210 by disposing the guide roller to allow the distance L1, in which the elastic member 10 is separated from the guide groove 114b and inserted into the groove 214 of the anvil roll 210, to be 30 mm or less. As a result, the function of preventing cutting of the elastic member 10 can be improved.

(B)

Although in the above embodiment, there is described the bonding device that performs ultrasonic welding and generates frictional heat by applying ultrasonic vibration to the sheets 2a, 2b to heat the sheets 2a, 2b, a specific configuration of heating and welding the sheets 2a, 2b is not limited thereto. As another modification of the present invention, for example, a device that heats and welds the sheets 2a, 2b without vibrating them may be used as a bonding device to heat and weld the sheets 2a, 2b in the step of bonding without vibrating them, as in so-called heat sealing.

(C)

Although in the above embodiment, the guide plate 112 is fixed to a fixing member 113, which is fixed to a panel or the like inside the apparatus, by screwing or the like to be prevented from being displaced as illustrated in FIGS. 10A and 10B, the present invention is not limited thereto.

Figure 17:
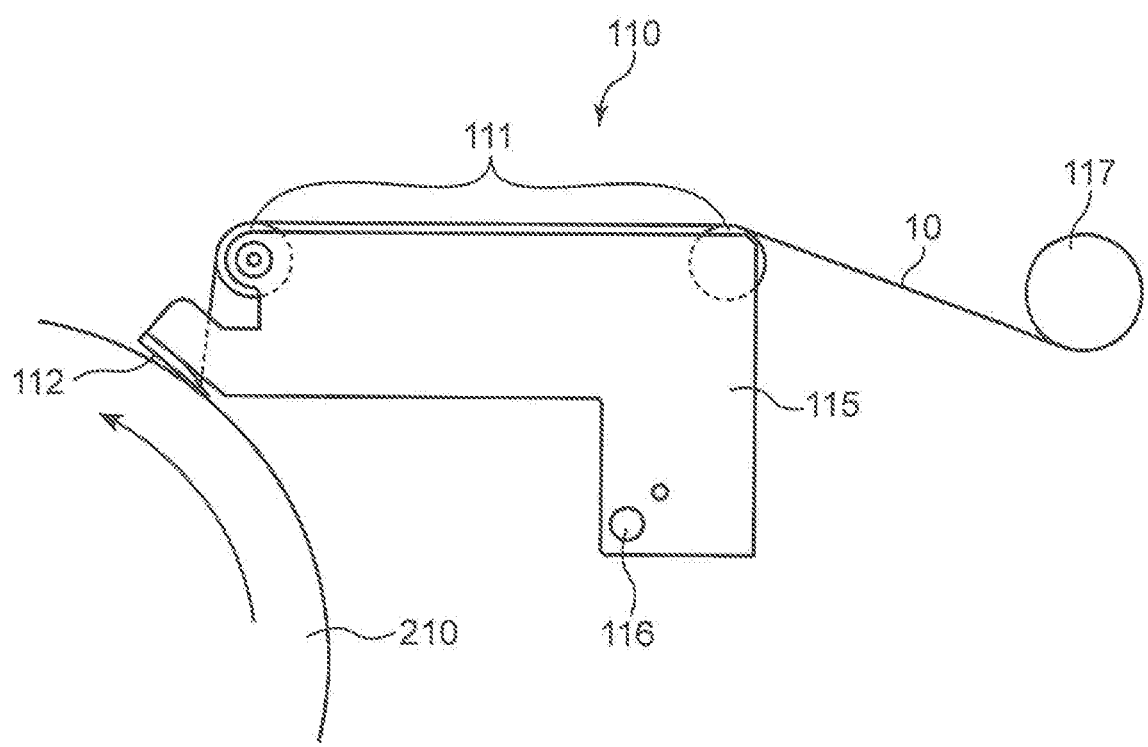
FIG. 17 is a view illustrating a manufacturing apparatus according to a modification of the present invention, being configured such that a guide plate is movable between a position close to an anvil roll and a position away from the anvil roll, and is a view illustrating a state in which the guide plate is at the position close to the anvil roll (position during operation of the manufacturing apparatus).
Figure 18:
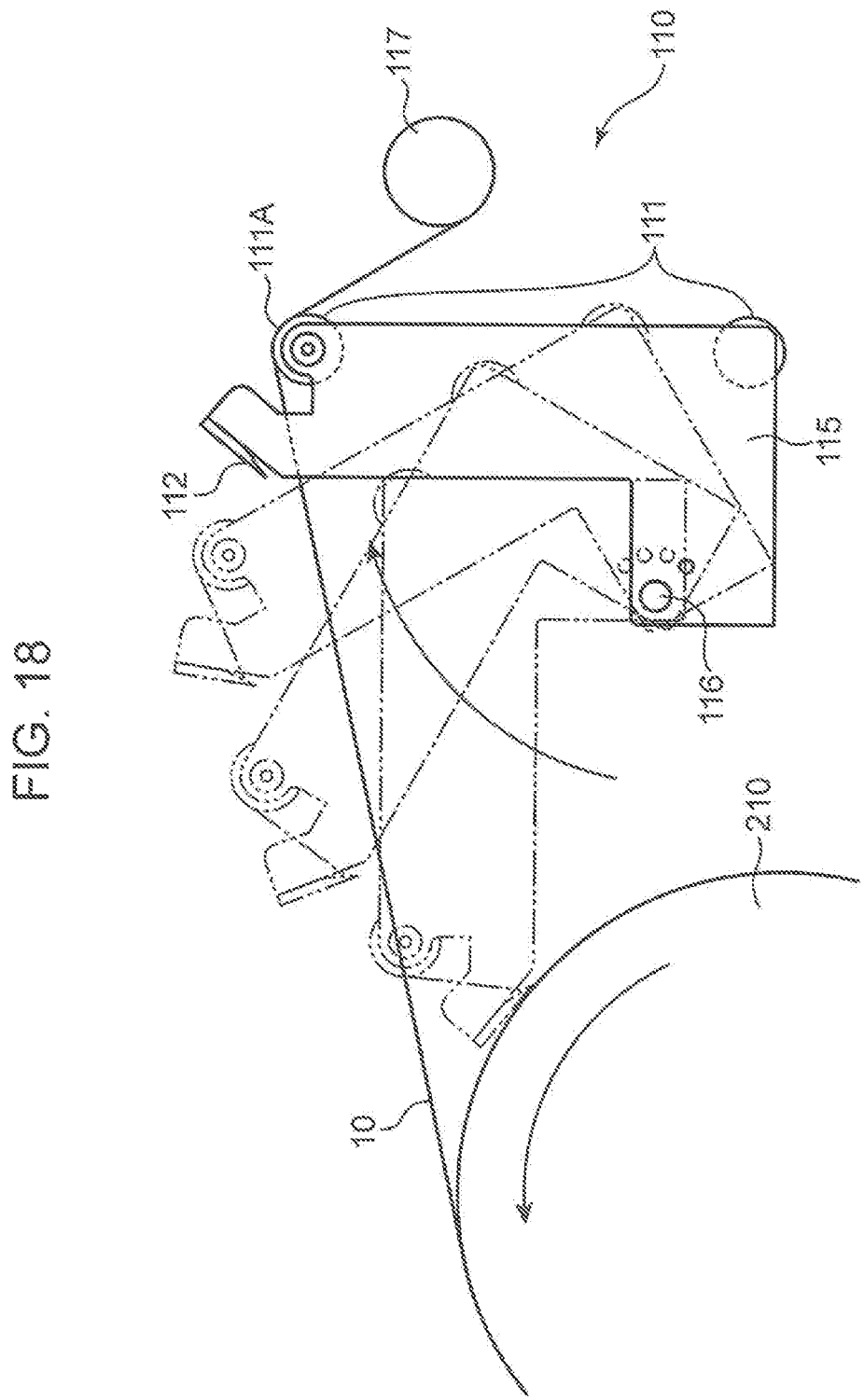
FIG. 18 is a view illustrating a state in which the guide plate of FIG. 17 is at the position away from the anvil roll (a position when an elastic member such as a rubber thread is allowed to pass).

As still another modification of the present invention, the guide plate 112 may be configured to be movable between a position close to the anvil roll 210 (conveying roller) illustrated in FIG. 17 and a position away from the anvil roll 210 illustrated in FIG. 18.

Specifically, the elastic member guide device 110 illustrated in FIG. 17 to 18 includes not only the multiple guide rolls 111 and the guide plate 112, but also a holding member 115 that holds both of the guide rolls 111 and the guide plate 112, a support shaft 116 that supports the holding member 115 to be swingable vertically, and a supply roll 117 disposed on upstream of the guide rolls 111 in the conveying direction of the elastic member 10. The support shaft 116 and a rotation shaft of the supply roll 117 are fixed at a predetermined position inside the manufacturing apparatus 100 to be prevented from being displaced. The multiple guide rolls 111 and the supply roll 117 are each provided in its outer peripheral surface with a groove for guiding the elastic member 10.

As illustrated in FIGS. 17 to 18, when the holding member 115 holding the guide rolls 11I and the guide plate 112 swings vertically on the support shaft 116 as a rotation center, the guide plate 112 can move between a position close to the anvil roll 210 (conveying roller) illustrated in FIG. 17 and a position away from the anvil roll 210 illustrated in FIG. 18.

As illustrated in FIG. 17, when the guide plate 112 is at the position close to the anvil roll 210 (i.e., the position during operation of the manufacturing apparatus 100), the elastic member 10 is pressed by the guide plate 112 from above and moved from the supply roll 117 to the multiple guide rolls 111, and the guide plate 112 in this order to be fed onto the outer peripheral surface of the anvil roll 210.

In contrast, as illustrated in FIG. 18, when the guide plate 112 is at the position away from the anvil roll 210 (the position allowing the elastic member 10 such as a rubber thread to pass), the guide plate 112 is retracted upward from the elastic member 10. This enables facilitating work of setting the elastic member 10 in the guide device 110, specifically, work of stretching the elastic member 10 between the groove of the guide roll 111A positioned most downstream of the multiple guide rolls 111 and the outer periphery of the anvil roll 210. When the guide plate 112 is returned to the position close to the anvil roll 210 illustrated in FIG. 17 again after the elastic member 10 is set in the guide device 110, the elastic member 10 is inserted into the groove 114b (see FIG. 10B) of the guide plate 112 and is placed in the groove of each of the guide rolls 111. This enables the guide device 110 to return to the state illustrated in FIG. 17.

Summary of Embodiment

The above embodiment is summarized as follows.

The manufacturing apparatus for manufacturing a composite stretchable member according to the above embodiment is a manufacturing apparatus for manufacturing a composite stretchable member including the two sheets and the multiple elastic members sandwiched between the two sheets by bonding the two sheets to each other and bonding the sheets to the multiple elastic members while conveying each of the sheets in a longitudinal direction thereof, the manufacturing apparatus comprising: a bonding device that welds and bonds the multiple elastic members to the two sheets, and the two sheets to each other, while the multiple elastic members are sandwiched between the two sheets being conveyed; and a guide device that guides the two sheets and the multiple elastic members to the bonding device in such a manner that each of the multiple elastic members extends in a longitudinal direction thereof and is sandwiched between the two sheets, wherein: the bonding device includes: a conveying roller that has an outer peripheral surface used for conveying the two sheets sandwiching the multiple elastic members in the longitudinal direction of each of the two sheets and that rotates about an axis predetermined; and a compressing device that faces the outer peripheral surface of the conveying roller to compress the two sheets sandwiching the multiple elastic members between the outer peripheral surface of the conveying roller and the compressing device; the bonding device is configured to apply heat to the two sheets between the conveying roller and the compressing device; the outer peripheral surface of the conveying roller is provided with at least one protruding section formed protruding radially outward from the outer peripheral surface; the at least one protruding section includes multiple grooves extending in a conveying direction of the conveying roller and being away from each other in a direction parallel to the axis; the guide device includes a guide member provided with a leading end closest to the outer peripheral surface of the conveying roller, and the multiple guide grooves, provided in the leading end, for holding the corresponding multiple elastic members, in a state where the multiple elastic members are away from each other in a direction parallel to the axis of the conveying roller, to guide the multiple elastic members into the corresponding multiple grooves of the conveying roller, and the guide member is disposed to allow each of the multiple elastic members positioned between the guide grooves and the corresponding grooves of the conveying roller to have a length of 30 mm or less.

As a result of intensive studies on a technique in which the elastic member is reliably guided by the guide member without being detached from the groove in the outer peripheral surface of the conveying roller, the present inventors have found that when a distance in which the elastic member moves in the air between the guide groove of the guide member and the groove of the conveying roller, i.e., a free distance of the elastic member, is reduced to a predetermined distance or less, the elastic member can be reliably guided to the groove of the conveying roller and can be prevented from being detached from the groove, and thus having fabricated the manufacturing apparatus.

That is, the manufacturing apparatus described above is configured such that disposing the guide member to allow the elastic member positioned between the guide groove and the groove of the conveying roller to have a length of 30 mm or less enables reducing the defect in which the elastic member is detached from the groove of the conveying roller when the elastic member is fed from the guide groove to the groove of the conveying roller. As a result, the function of preventing cutting of the elastic member 10 can be improved.

The manufacturing apparatus for manufacturing a composite stretchable member described above is preferably configured such that the guide member is disposed to allow the elastic members positioned between the guide grooves and the corresponding grooves of the conveying roller to each have a length of 15 mm or less.

The configuration described above enables reducing the defect in which the elastic member is detached from the groove of the conveying roller when the elastic member is fed from the guide groove to the groove of the conveying roller by disposing the guide member to allow the elastic member positioned between the guide groove and the groove of the conveying roller to have a length of 15 mm or less. As a result, the function of preventing cutting of the elastic member 10 can be further improved.

The manufacturing apparatus for manufacturing a composite stretchable member described above is preferably configured such that the guide member is disposed to allow a shortest distance between a bottom of each of the guide grooves and an outer peripheral surface of the protruding section of the conveying roller to be 1 mm or less.

The configuration described above enables the guide groove to approach the outer peripheral surface of the protruding section of the conveying roller, and thus enables shortening a distance in which the elastic member leaves the guide groove and is inserted into the groove of the conveying roller. This enables further reducing the defect in which the elastic member is detached from the groove of the conveying roller. As a result, the function of preventing cutting of the elastic member can be further improved.

The manufacturing apparatus for manufacturing a composite stretchable member described above is preferably configured such that the guide member is formed in a plate-like shape, the leading end is an edge of the guide member in a plate-like shape, the edge being closest to the outer peripheral surface of the conveying roller and having a tapered shape, and the multiple guide grooves are formed at the leading end tapered.

The configuration described above enables the guide member to be disposed close to the outer peripheral surface of the conveying roller without interfering with the conveying roller and the sheet wound around the outer peripheral surface of the conveying roller, by using the guide member in a plate-like shape with the leading end tapered. This enables further reducing the defect in which the elastic member is detached from the groove of the conveying roller, by shortening the distance between the guide groove and the groove of the anvil roll. The guide groove is formed at the leading end tapered, so that frictional resistance between the elastic member and the guide member when the elastic member passes through the guide groove can be reduced. As a result, the function of preventing cutting of the elastic member can be further improved.

The manufacturing apparatus for manufacturing a composite stretchable member described above is preferably configured such that the leading end of the guide member is disposed upstream of a contact point at which the elastic members are in contact with the outer peripheral surface of the conveying roller in a rotation direction of the conveying roller, the leading end of the guide member facing upstream, and the guide plate is disposed to allow a surface of the guide plate facing the conveying roller to form an angle of 30 degrees or less with respect to a tangent line of the conveying roller at the contact point.

The configuration described above enables the bottom of the guide groove to approach the outer peripheral surface of the conveying roller, and thus enables shortening a distance in which the elastic member leaves the guide groove and is inserted into the groove of the conveying roller. This enables further reducing the defect in which the elastic member is detached from the groove of the conveying roller. As a result, the function of preventing cutting of the elastic member can be further improved.

The manufacturing apparatus for manufacturing a composite stretchable member described above preferably further includes a nip roll that is disposed upstream of the compressing device in the conveying direction of the sheet to sandwich the two sheets and the elastic members in cooperation with the conveying roller in a region where the elastic members are inserted into the corresponding grooves of the conveying roller.

The configuration described above enables further reducing a defect in which the elastic member inserted into the groove of the conveying roller is detached from the groove of the conveying roller before reaching the compressing device. As a result, the function of preventing cutting of the elastic member can be further improved. Additionally, even when the elastic member contracts and tries to return when the elastic member is cut downstream of the nip roll, return of the elastic member is prevented because an end portion of the elastic member is sandwiched between the nip roll and the conveying roller. This facilitates restoration work of the manufacturing apparatus.

The manufacturing apparatus for manufacturing a composite stretchable member described above preferably further includes a guide roll that is disposed upstream of the guide member in the conveying direction of the elastic members to guide the elastic members into the corresponding guide grooves.

The configuration described above enables the elastic member to be reliably guided to the guide groove, so that the defect in which the elastic member is detached from the guide groove can be prevented.

The manufacturing apparatus for manufacturing a composite stretchable member described above is preferably configured such that the guide roll is disposed to allow a distance in which the elastic members are separated from the guide roll and inserted into the corresponding guide grooves to be 50 mm or more.

The configuration described above enables eliminating influence on the elastic member due to rotation unevenness and rattling of the guide roll, such as a slack of the elastic member.

The manufacturing apparatus for manufacturing a composite stretchable member described above is preferably configured such that a conveying distance from a position where the guide member comes into contact with the corresponding grooves of the conveying roller to a position where the guide member is compressed by the compressing device is 150 mm or less.

The configuration described above enables reducing a defect in which the elastic member is detached from the groove of the conveying roller while the elastic member is compressed by the compressing device after coming into contact with the groove of the conveying roller. As a result, the function of preventing cutting of the elastic member can be further improved.

The manufacturing apparatus for manufacturing a composite stretchable member described above is preferably configured such that the guide member is movable between a position close to the conveying roller and a position away from the conveying roller.

The configuration described above enables facilitating work of setting the elastic member in the guide device by moving the guide member to the position away from the conveying roller.

As described above, the manufacturing apparatus for manufacturing a composite stretchable member of the present embodiment enables improving the function of preventing cutting by reducing the defect in which the elastic member is detached from the groove of the conveying roller.

The invention claimed is:

1. A manufacturing apparatus for manufacturing a composite stretchable member including two sheets and multiple elastic members sandwiched between the two sheets by bonding the two sheets to each other and bonding the sheets to the multiple elastic members while conveying each of the sheets in a longitudinal direction thereof, the manufacturing apparatus comprising:
   a bonding device that welds and bonds the multiple elastic members to the two sheets, and the two sheets to each other, while the multiple elastic members are sandwiched between the two sheets being conveyed; and
   a guide device that guides the two sheets and the multiple elastic members to the bonding device in such a manner that each of the multiple elastic members extends in a longitudinal direction thereof and is sandwiched between the two sheets, wherein:
   the bonding device includes:
   a conveying roller that has an outer peripheral surface used for conveying the two sheets sandwiching the multiple elastic members in the longitudinal direction of each of the two sheets and that rotates about an axis predetermined; and
   a compressing device that faces the outer peripheral surface of the conveying roller to compress the two sheets sandwiching the multiple elastic members between the outer peripheral surface of the conveying roller and the compressing device;
   the bonding device is configured to apply heat to the two sheets between the conveying roller and the compressing device;
   the outer peripheral surface of the conveying roller is provided with at least one protruding section formed protruding radially outward from the outer peripheral surface;
   the at least one protruding section includes multiple grooves extending in a conveying direction of the conveying roller and being away from each other in a direction parallel to the axis;
   the guide device includes a guide member provided with a leading end closest to the outer peripheral surface of the conveying roller, and multiple guide grooves, provided in the leading end, for holding the corresponding multiple elastic members, in a state where the multiple elastic members are away from each other in a direction parallel to the axis of the conveying roller, to guide the multiple elastic members into the corresponding multiple grooves of the conveying roller, the guide member is disposed to allow each of the multiple elastic members positioned between the guide grooves and the corresponding grooves of the conveying roller to have a length within a range of 1 mm to 30 mm, and the leading end of the guide member is disposed upstream of a contact point at which the elastic members are in contact with the outer peripheral surface of the conveying roller in a rotation direction of the conveying roller, the elastic members engaged into the respective guide grooves are bent at bottoms of the respective guide grooves, and each of the elastic members extends in a tangential direction of the contact point on the outer peripheral surface of the conveying roller and is inserted into the corresponding one of the grooves at the contact point on the outer peripheral surface of the conveying roller.

2. The manufacturing apparatus for manufacturing a composite stretchable member according to claim 1, wherein the guide member is disposed to allow the elastic members positioned between the guide grooves and the corresponding grooves of the conveying roller to each have a length of 15 mm or less.

3. The manufacturing apparatus for manufacturing a composite stretchable member according to claim 1, wherein the guide member is disposed to allow a shortest distance between a bottom of each of the guide grooves and an outer peripheral surface of the protruding section of the conveying roller to be 1 mm or less.

4. The manufacturing apparatus for manufacturing a composite stretchable member according to claim 1, wherein the guide member is formed in a plate shape, the leading end is an edge of the guide member in a plate shape, the edge being closest to the outer peripheral surface of the conveying roller and having a tapered shape, and the multiple guide grooves are formed at the leading end tapered.

5. The manufacturing apparatus for manufacturing a composite stretchable member according to claim 4, wherein the leading end of the guide member is disposed upstream of a contact point at which the elastic members are in contact with the outer peripheral surface of the conveying roller in a rotation direction of the conveying roller, the leading end of the guide member facing upstream, and the guide plate is disposed to allow a surface of the guide member facing the conveying roller to form an angle of 30 degrees or less with respect to a tangent line of the conveying roller at the contact point.

6. The manufacturing apparatus for manufacturing a composite stretchable member according to claim 1, further comprising:

a nip roll that is disposed upstream of the compressing device in the conveying direction of the sheet to sandwich the two sheets and the elastic members in cooperation with the conveying roller in a region where the elastic members are inserted into the corresponding grooves of the conveying roller.

7. The manufacturing apparatus for manufacturing a composite stretchable member according to claim 1, further comprising:

a guide roll that is disposed upstream of the guide member in the conveying direction of the elastic members to guide the elastic members into the corresponding guide grooves.

8. The manufacturing apparatus for manufacturing a composite stretchable member according to claim 7, wherein the guide roll is disposed to allow a distance in which the elastic members are separated from the guide roll and inserted into the corresponding guide grooves to be 50 mm or more.

9. The manufacturing apparatus for manufacturing a composite stretchable member according to claim 1, wherein a conveying distance from a position where the elastic member comes into contact with the corresponding grooves of the conveying roller to a position where the elastic member is compressed by the compressing device is 150 mm or less.

10. The manufacturing apparatus for manufacturing a composite stretchable member according to claim 1, wherein the guide member is movable between a position close to the conveying roller and a position away from the conveying roller.

11. The manufacturing apparatus for manufacturing a composite stretchable member according to claim 2, wherein the guide member is disposed to allow a shortest distance between a bottom of each of the guide grooves and an outer peripheral surface of the protruding section of the conveying roller to be 1 mm or less.

12. The manufacturing apparatus for manufacturing a composite stretchable member according to claim 6, further comprising:

a guide roll that is disposed upstream of the guide member in the conveying direction of the elastic members to guide the elastic members into the corresponding guide grooves.

13. The manufacturing apparatus for manufacturing a composite stretchable member according to claim 2, wherein a conveying distance from a position where the elastic member comes into contact with the corresponding grooves of the conveying roller to a position where the elastic member is compressed by the compressing device is 150 mm or less.

14. The manufacturing apparatus for manufacturing a composite stretchable member according to claim 3, wherein a conveying distance from a position where the elastic member comes into contact with the corresponding grooves of the conveying roller to a position where the elastic member is compressed by the compressing device is 150 mm or less.

15. The manufacturing apparatus for manufacturing a composite stretchable member according to claim 4, wherein a conveying distance from a position where the elastic member comes into contact with the corresponding grooves of the conveying roller to a position where the elastic member is compressed by the compressing device is 150 mm or less.

16. The manufacturing apparatus for manufacturing a composite stretchable member according to claim 6, wherein a conveying distance from a position where the elastic member comes into contact with the corresponding grooves of the conveying roller to a position where the elastic member is compressed by the compressing device is 150 mm or less.

17. The manufacturing apparatus for manufacturing a composite stretchable member according to claim 9, wherein
a conveying distance from a position where the elastic member comes into contact with the corresponding grooves of the conveying roller to a position where the elastic member is compressed by the compressing device is 150 mm or less.

18. The manufacturing apparatus for manufacturing a composite stretchable member according to claim 6, wherein
the guide member is movable between a position close to the conveying roller and a position away from the conveying roller.

19. The manufacturing apparatus for manufacturing a composite stretchable member according to claim 7, wherein
the guide member is movable between a position close to the conveying roller and a position away from the conveying roller.

20. The manufacturing apparatus for manufacturing a composite stretchable member according to claim 9, wherein
the guide member is movable between a position close to the conveying roller and a position away from the conveying roller.

* * * * *